United States Patent
Campisi et al.

(10) Patent No.: US 9,889,226 B2
(45) Date of Patent: Feb. 13, 2018

(54) PHOTOCROSSLINKED HYALURONIC ACID DERIVATIVES, AND THE PREPARATION PROCESS AND USE THEREOF

(71) Applicant: FIDIA FARMACEUTICI S.P.A., Abano Terme (IT)

(72) Inventors: Monica Campisi, Abano Terme (IT); Ottorino De Lucchi, Abano Terme (IT); Riccardo Beninatto, Abano Terme (IT); Giuseppe Borsato, Abano Terme (IT)

(73) Assignee: FIDIA FARMACEUTICI S.P.A., Abano Terme (PD) (IT)

( * ) Notice: Subject to any disclaimer, the term of this patent is extended or adjusted under 35 U.S.C. 154(b) by 8 days.

(21) Appl. No.: 14/765,783

(22) PCT Filed: Feb. 4, 2014

(86) PCT No.: PCT/IB2014/058784
§ 371 (c)(1),
(2) Date: Aug. 4, 2015

(87) PCT Pub. No.: WO2014/122580
PCT Pub. Date: Aug. 14, 2014

(65) Prior Publication Data
US 2015/0367027 A1     Dec. 24, 2015

(30) Foreign Application Priority Data
Feb. 6, 2013  (IT) .............. MI2013A0162

(51) Int. Cl.
| | |
|---|---|
| *A61L 27/20* | (2006.01) |
| *C08B 37/08* | (2006.01) |
| *A61L 27/52* | (2006.01) |
| *A61L 27/26* | (2006.01) |
| *A61L 27/38* | (2006.01) |
| *A61L 27/54* | (2006.01) |
| *A61L 27/56* | (2006.01) |
| *A61K 47/61* | (2017.01) |
| *A61K 47/69* | (2017.01) |

(52) U.S. Cl.
CPC .............. *A61L 27/20* (2013.01); *A61K 47/61* (2017.08); *A61K 47/6903* (2017.08); *A61L 27/26* (2013.01); *A61L 27/3804* (2013.01); *A61L 27/52* (2013.01); *A61L 27/54* (2013.01); *A61L 27/56* (2013.01); *C08B 37/0072* (2013.01); *A61L 2300/64* (2013.01); *A61L 2400/16* (2013.01); *A61L 2430/06* (2013.01)

(58) Field of Classification Search
None
See application file for complete search history.

(56) References Cited

U.S. PATENT DOCUMENTS

| | | | |
|---|---|---|---|
| 6,005,093 A * | 12/1999 | Wood | C07D 311/16 536/24.3 |
| 2009/0028946 A1 * | 1/2009 | Sheardown | A61K 41/0028 424/487 |

FOREIGN PATENT DOCUMENTS

| | | |
|---|---|---|
| EP | 1 519 962 A1 | 4/2005 |
| WO | WO 03/076475 A1 | 9/2003 |

OTHER PUBLICATIONS

Ifkovits, J. L., & Burdick, J. A. (2007). Review: photopolymerizable and degradable biomaterials for tissue engineering applications. Tissue engineering, 13(10), 2369-2385.*
International Search Report, issued in PCT/IB2014/058784, dated Apr. 24, 2014.
Written Opinion of the International Searching Authority, issued in PCT/IB2014/058784, dated Apr. 24, 2014.

* cited by examiner

*Primary Examiner* — Shaojia A Jiang
*Assistant Examiner* — Dale R Miller
(74) *Attorney, Agent, or Firm* — Birch, Stewart, Kolasch & Birch, LLP

(57) ABSTRACT

Disclosed are photocrosslinked hyaluronic acid (HA) derivatives consisting of HA, a bifunctional polyethylene glycol (PEG) spacer which is triethylene glycol, and a photoreactive compound selected from a coumarin derivative and propiophenone.

20 Claims, 11 Drawing Sheets

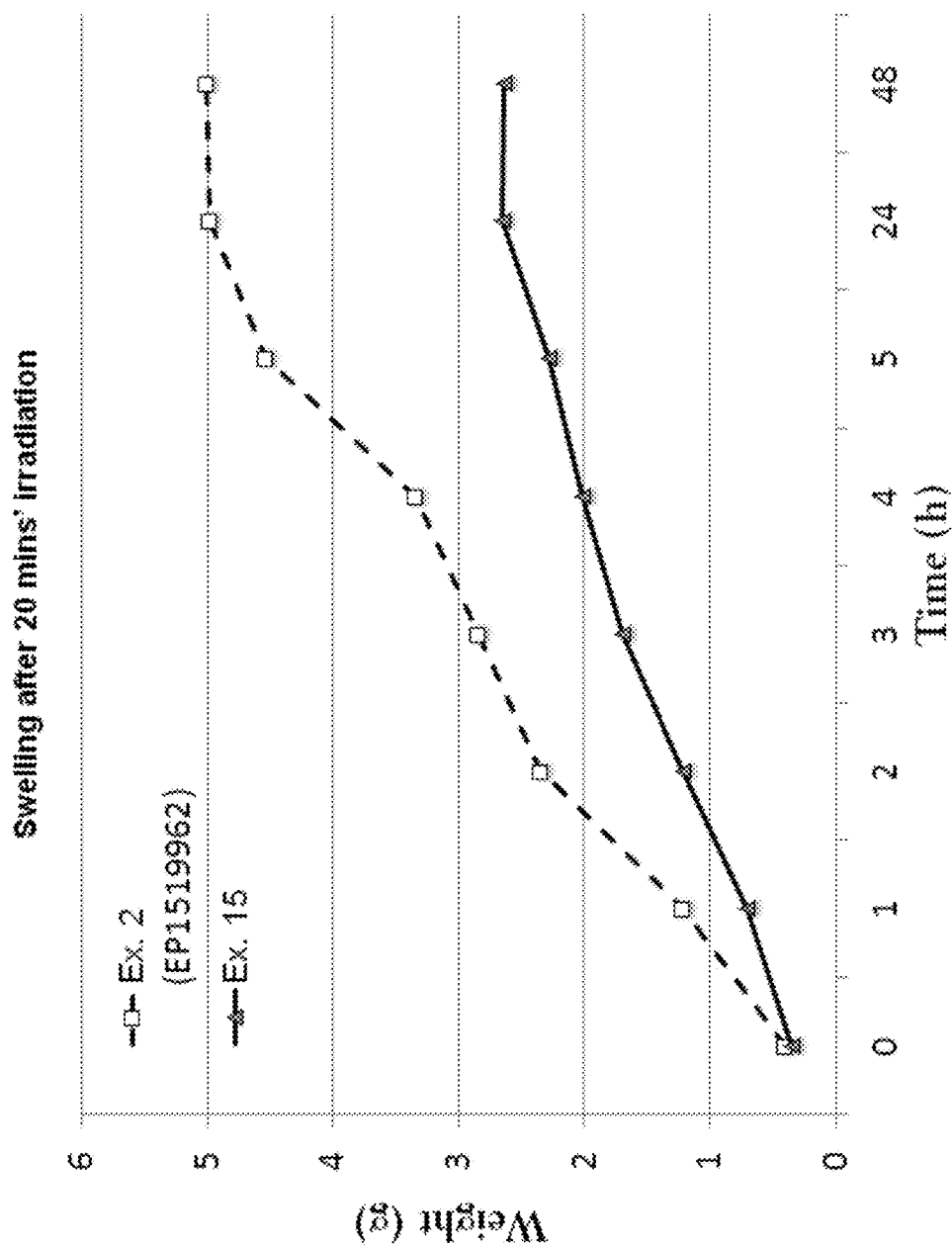
FIGURE 8: Degree of swelling of hydrogels prepared as in Example 15 of the present patent and Example 2 of patent EP1519962

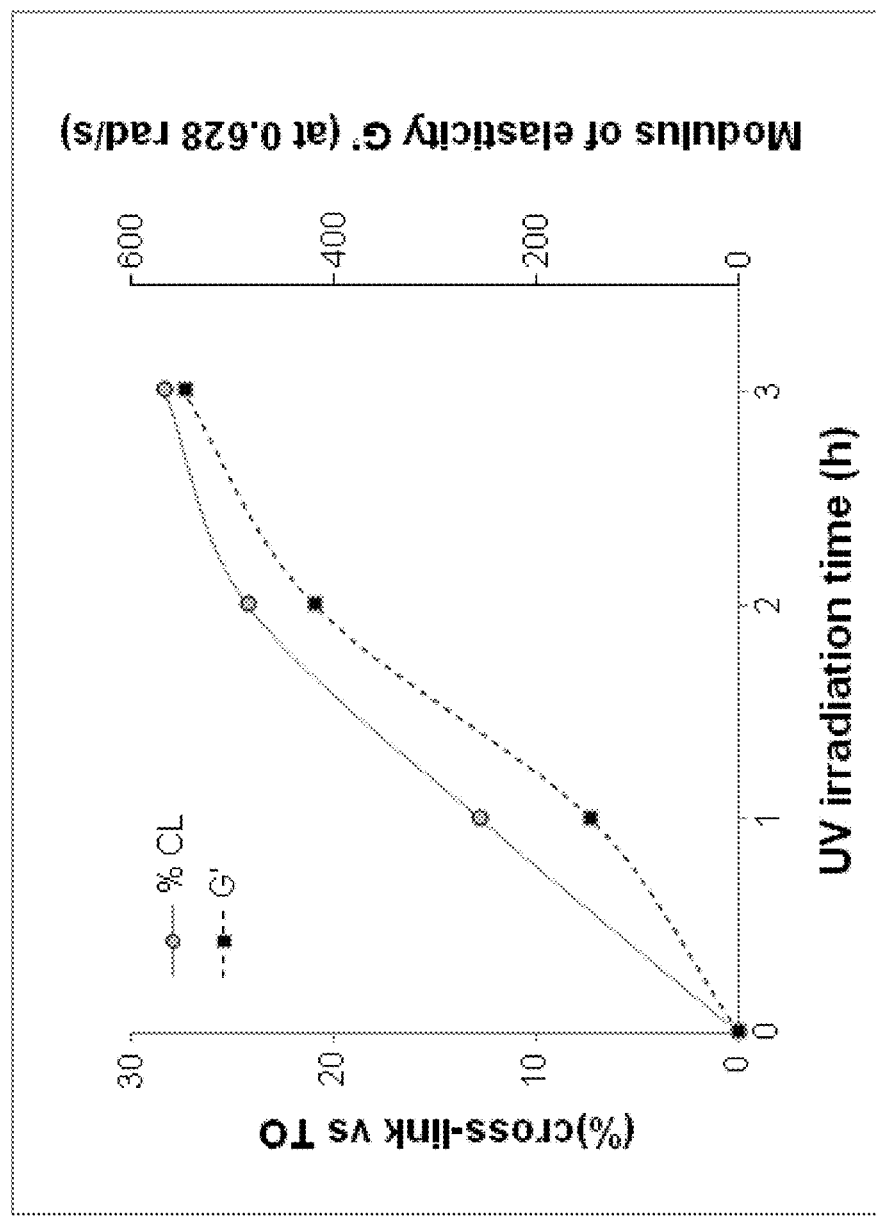
FIGURE 9: (1) Crosslinking (% CL) and (2) G' according to the irradiation time of (9)

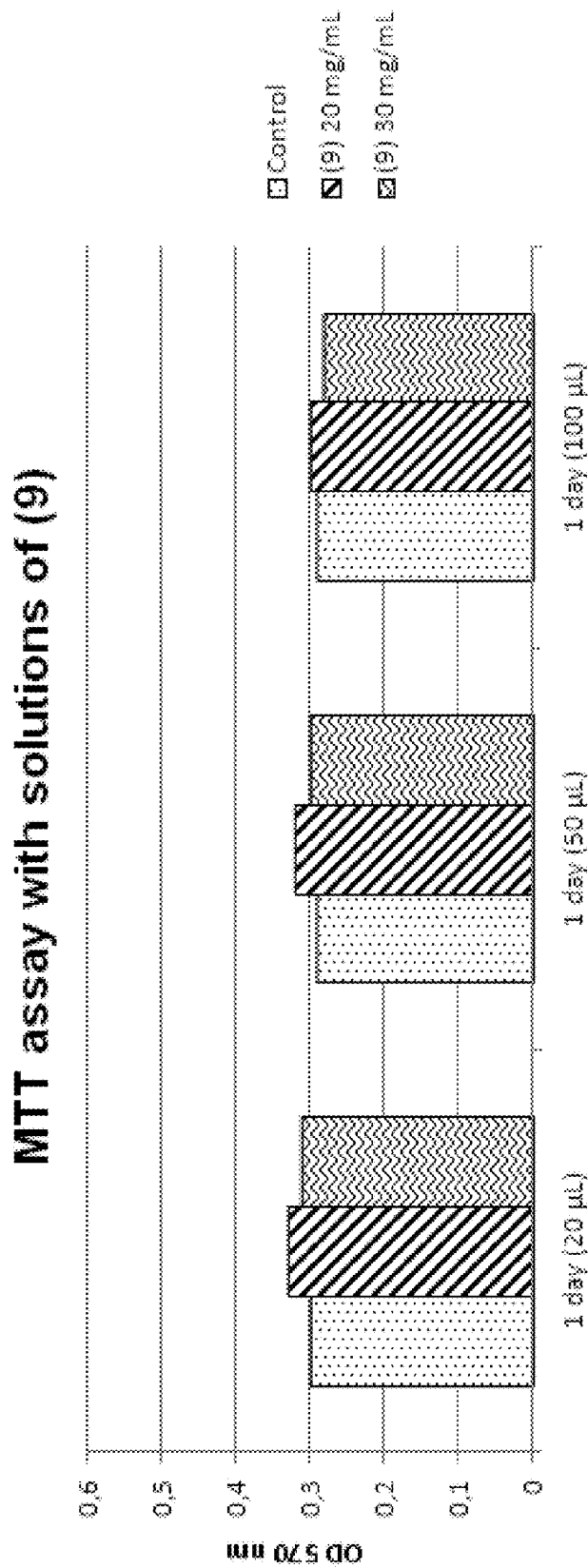
FIGURE 10: MTT assay with solutions of (9) after one day's incubation with HF

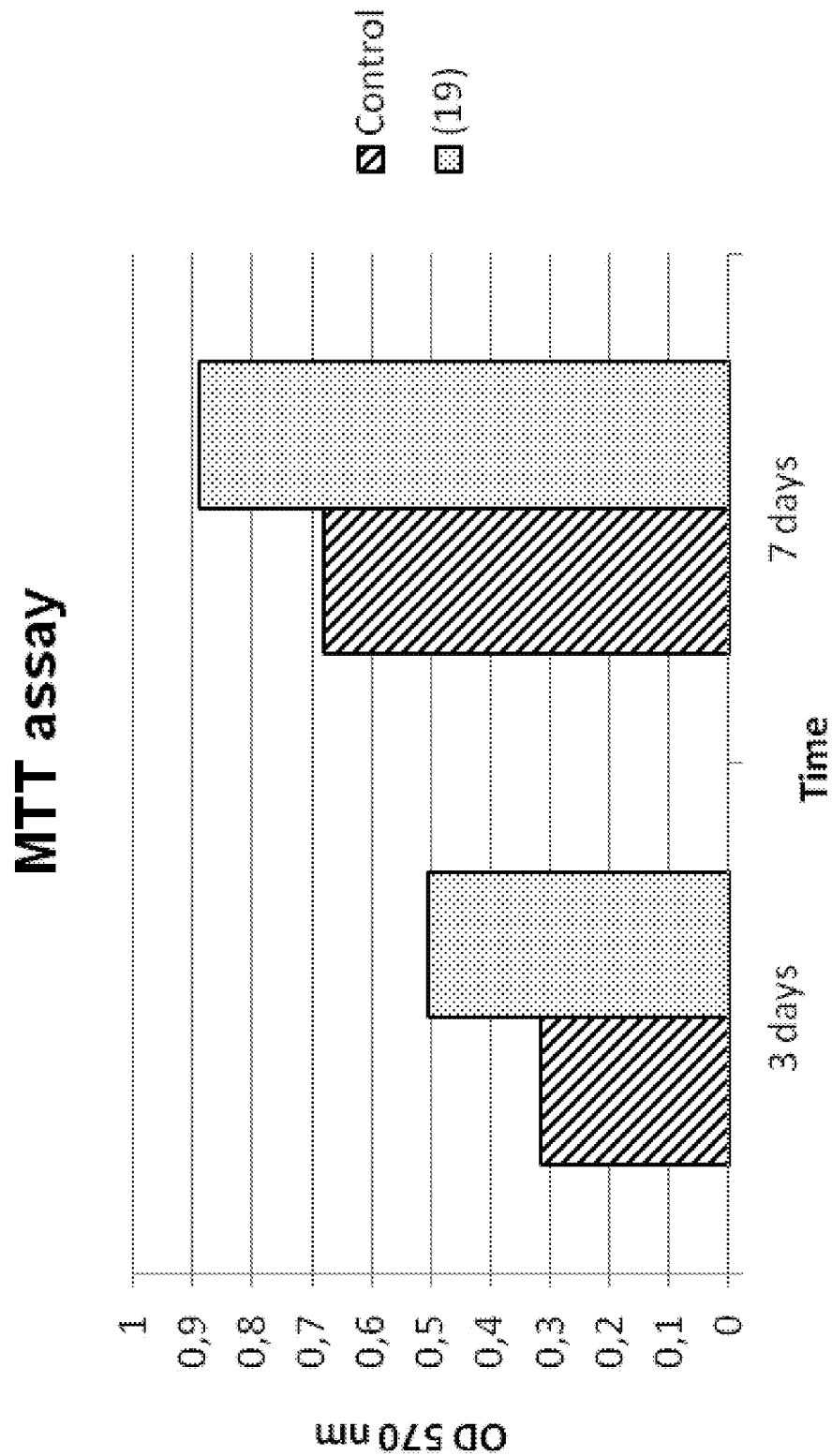
FIGURE 11: MTT assay of HF seeded on a sponge prepared as in example 19.

PHOTOCROSSLINKED HYALURONIC ACID DERIVATIVES, AND THE PREPARATION PROCESS AND USE THEREOF

SUMMARY OF THE INVENTION

The present invention discloses photocrosslinked hyaluronic acid (HA) derivatives consisting of HA, a bifunctional polyethylene glycol (PEG) spacer which is triethylene glycol, and a photoreactive compound selected from a coumarin derivative and propiophenone.

TECHNICAL BACKGROUND

Hydrogels and sponges are polymer networks characterised by a three-dimensional structure, which is compact in the case of hydrogels and has interconnected pores in the case of sponges. Sponges normally absorb a great deal of water, whereas this characteristic ("swelling") may be less marked in hydrogels, depending on the compactness of the hydrogel; a very compact gel absorbs less water than one which is not very compact.

These types of materials have been studied for some time; for example, hydrogels are used in the fields of drug delivery, soft tissue filling, and joint disorders that benefit from the insertion into the joint of "bearings" that absorb tensions and shocks. Sponges are used in particular in the field of tissue engineering, especially for their ability to be colonised by cells. The applications obviously depend entirely on the nature of the starting polymer used. Specifically in the case of the present invention, the polymer chosen is a polysaccharide, namely hyaluronic acid (HA), a heteropolysaccharide consisting of alternating residues of D-glucuronic acid and N-acetyl-D-glucosamine. It is a linear-chain polymer with a molecular weight of up to $13 \times 10^6$ Da, depending on the source from which it is obtained and the preparation methods used. It is ubiquitously present and plays an important role in the biological organism, especially as a mechanical support for the cells of many tissues, such as skin, tendons, muscles and cartilage. It also modulates many different processes relating to cell physiology and biology, such as cell proliferation, migration and differentiation and angiogenesis (Weigel P. et al., *J Theoretical Biol*, 1986:219-234; Abatangelo G. et al., *J Surg Res*, 1983, 35:410-416; Goa K. et al., *Drugs*, 1994, 47:536-566), and also performs other functions, such as tissue hydration and joint lubrication. In the joints, the hyaluronic acid contained in the synovial fluid acts as a viscous lubricant during slow movements, while during fast movements, due to its elastic properties, it absorbs any traumas or microtraumas affecting the joint (Balazs EA. et al., J Rheumatol Suppl, 1993, 12:75-82; Belcher C. et al., Annals of the Rheumatic Diseases, 1997, 56:299-307). The combination of these properties, which are widely recognised, has been exploited for some time in the preparation of dressings used in the treatment of wounds, ulcers and skin lesions of various origins, and in medical devices designed for intra-articular application for the treatment of osteoarthritis, cartilage degeneration, etc.

Numerous methods are used to obtain hydrogels with specific characteristics from various polysaccharides; the most important used successfully on hyaluronic acid include chemical crosslinking, using molecules (divinyl sulphone, BDDE) that specifically react with given functional groups, or free-radical polymerisation. These methods, which presuppose a chemical modification of HA to make them suitable for the subsequent crosslinking or polymerisation (derivatisation) reaction, give rise to hydrogels with good characteristics of compactness, chemical and mechanical resistance and hydratability; however, as the derivatisation and crosslinking take place simultaneously, reagent residues can be retained in their structure during the formation of the gel, and are very often toxic because they are difficult to eliminate.

Another system for obtaining the formation of a polymer crosslink is the use of UV radiation on polysaccharides previously derivatised with suitable functional groups to render them photoreactive. Derivatisation involves bonding to the polysaccharide substances which, when activated by UV radiation, bond together, crosslinking the different polymer chains and thus creating the network. Said process is particularly advantageous because it allows easy, effective elimination of undesirable reaction residues or intermediates during the derivatisation step, and therefore helps to make the end product safer. Numerous photoreactive substances can be used; for example, both hydrogels (EP0554898; U.S. Pat. No. 6,602,859) and sponges (EP1666503) obtained from HA derivatised with cinnamic acid or thymine are known. In these cases, hyaluronic acid is bonded to the cinnamic acid or thymine residue and then irradiated to obtain the hydrogel; for sponges, the hydrogel is freeze-dried or frozen, and then undergoes a second irradiation cycle. A further photoreactive substance which can be used is propiophenone; gels obtained from hyaluronic acid or derivatives thereof which are bonded via ester bonds to propiophenone and then irradiated are known (EP1519962). Other photoreactives known in the prior art are anthracene, riboflavin, coumarin and uracil, suitably derivatised and substituted, to promote the bond with the polysaccharide, which is normally the ester or amide type and therefore involves the —OH, —COOH and —NH$_2$ groups normally present in the polysaccharide. The polysaccharide is often derivatised before the reaction, for example to protect some functional groups or to promote the formation of the desired bond. The characteristics of hydrogels, such as compactness, hydratability, mechanical strength, etc., can be varied by modulating the various parameters (type of polysaccharide, photoreactive, bond between the two entities, percentage of photoreactive compared with polysaccharide, intensity and duration of irradiation).

In the ambit of the present invention the Applicant has surprisingly discovered that hyaluronic acid bonded to particular photoreactive via a specific spacer produces, after suitable UV irradiation, hydrogels of excellent compactness which are biodegradable, biocompatible, non-toxic and have shape memory properties; in other words said hydrogels maintain the shape of the container in which they were prepared, and can be cut while retaining their structure, or otherwise very easily manipulated. The same characteristics also belong to the sponges claimed herein, and are obtained innovatively not from a hydrogel, as described to date by the prior art, but from a solution of hyaluronic acid bonded to the spacer and the photoreactive, subsequent freeze-drying, and finally UV irradiation; unlike known sponges, only a single irradiation step is therefore required, which represents a considerable industrial advantage. Sponges also possess shape memory, and can therefore be repeatedly soaked and squeezed while still maintaining the same shape and structure characteristics, and requiring a single UV irradiation. The Applicant has demonstrated that this set of characteristics is associated with the use of a particular spacer, which makes the invention new and inventive compared with the prior art.

In particular, Example 8 and FIG. 8 illustrate the comparative data for the degree of swelling between hydrogels prepared according to Example 2 of said prior patent EP1519962, owned by the Applicant, and hydrogels prepared according to Example 15 of the present patent application. As the latter hydrogels absorb less water they are more compact, and crosslinking is therefore more efficient.

BRIEF DESCRIPTION OF THE FIGURES

FIG. 8 shows the degree of swelling of hydrogels prepared as in Example 15 of the present patent and Example 2 of patent EP1519962.

FIG. 9 shows the (1) Crosslinking (% CL) and (2) G' according to the irradiation time of 7-(2-(2(2-iodoethoxy)ethoxy)ethoxy)-2H-chromen-2-one (Example 9).

FIG. 10 shows MTT assay results with solutions of 7-(2-(2(2-iodoethoxy)ethoxy)ethoxy)-2H-chromen-2-one (Example 9) after one day's incubation with HF.

FIG. 11 shows MTT assay results of HF seeded on a sponge prepared as in Example 19.

DETAILED DESCRIPTION OF THE INVENTION

Figure 1:
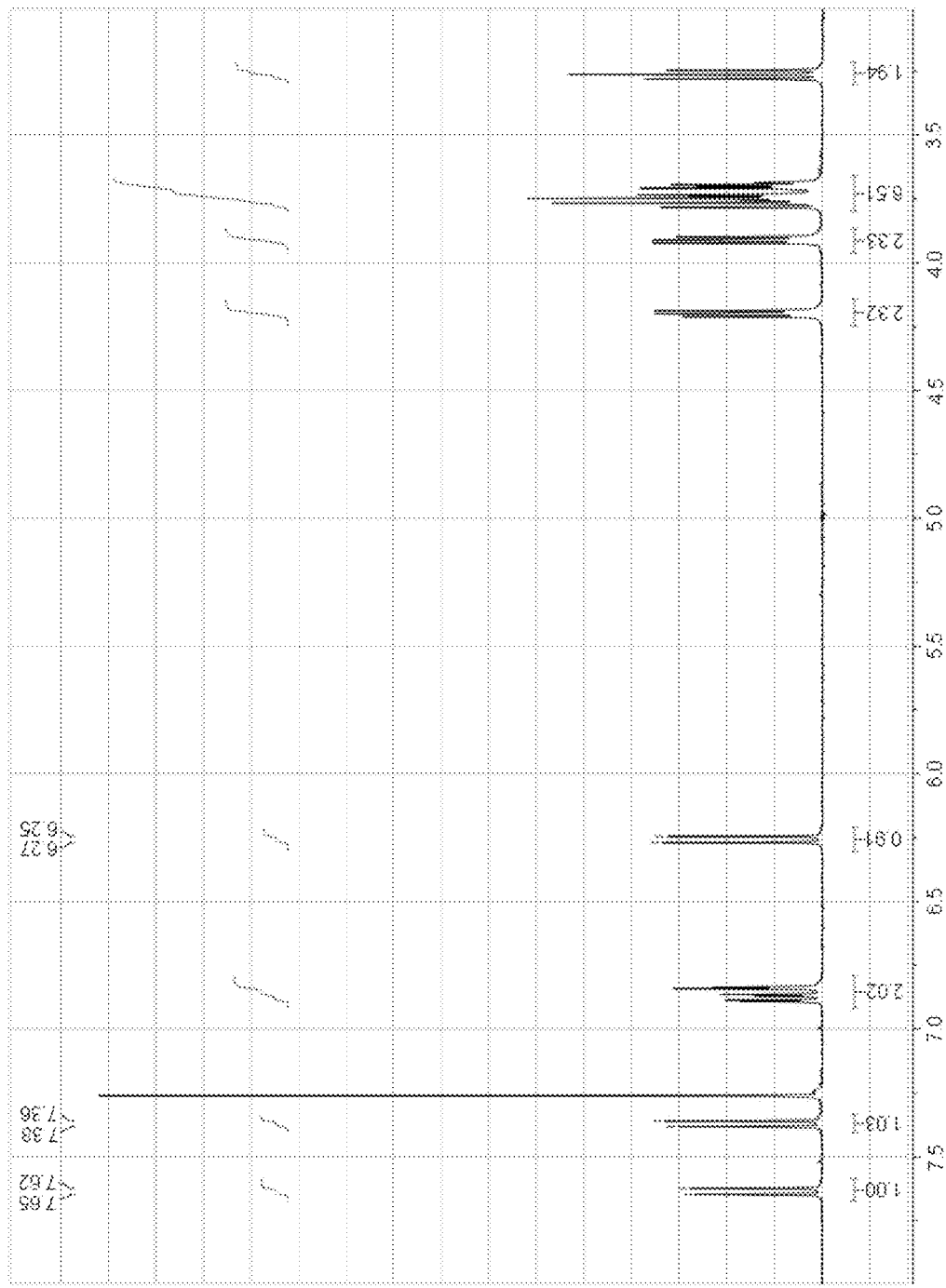
FIG. 1 shows the $^1$H NMR spectroscopic analysis of 7-(2-(2-(2-iodoethoxy)ethoxy)ethoxy)-2H-chromen-2-one (Example 3).

The present invention discloses and claims photocrosslinked derivatives of hyaluronic acid (HA), their preparation process by crosslinking based on UV irradiation of suitably prepared photocrosslinkable intermediates, and the use of said photocrosslinked derivatives in the medical field. The photocrosslinked derivatives described herein take the form of hydrogels with different degrees of compactness or sponges, namely three-dimensional structures with interconnected pores. They are biocompatible, biodegradable, non-toxic and, above all, their degree of compactness or porosity can be modulated. A further characteristic of these inventions is shape memory, namely the ability to maintain their shape even outside the container in which they were produced and, in the case of sponges, after repeated soaking and squeezing. The products according to the present invention can be applied in numerous medical and biomedical fields. Hydrogels, for example, can be used for:

the release of active ingredients encapsulated in or chemically bonded to them; the various active ingredients include pharmacologically and/or biologically active substances such as trophic factors, antibiotics, steroidal and non-steroidal anti-inflammatory drugs, proteins, peptides, hormones and platelet extracts;

coating objects for medical use;

encapsulating solid materials such as bone powders, coral granules, bioceramics and hydroxyapatite, with which pastes for use in the field of orthopaedic surgery, dentistry, etc. can be modelled;

filling defects of various sizes in soft tissues, such as wrinkles, depressed scars, and cavities deriving from surgery;

acting as scaffolds for cell growth and regeneration of tissue such as bone, adipose tissue, skin, cartilage, tendons, ligaments, muscle, nerve tissue, endothelial tissue, connective tissue, etc. Cells, whether differentiated or undifferentiated, can be inserted in the scaffold before implantation, and suitably cultured; alternatively, the scaffold can be inserted in the lesion to be treated, and left to be colonised by the cells physiologically present at the site of the lesion. For this type of application it can be particularly useful to mix the hyaluronic acid before irradiation with collagen which, remaining physically trapped in the hydrogel mesh formed, gives the hydrogel greater elasticity and improves its structural capacity and adaptation to the site where it will be positioned;

acting as a postoperative mechanical barrier against adhesions and protecting tissues against inflammatory damage;

treatment of osteoarthritis and/or cartilage damage by intra-articular injection. Once again, the hydrogel can contain differentiated or undifferentiated cells and/or pharmacologically or biologically active substances, as described above.

Sponges are especially useful in the field of tissue engineering (e.g. for skin, bone, cartilage, adipose tissue, tendons, ligaments, muscle, nerves, endothelium and connective tissue) due to their ability to house cells in their pores; as in the case of hydrogels, cells, whether differentiated or undifferentiated, can be inserted in the scaffold before implantation, and suitably cultured; alternatively, the scaffold can be inserted in the lesion to be treated, and left to be colonised by the cells physiologically present at the site of the lesion. Due to their structure, sponges are particularly suitable for reconstruction of tissue in cavitated and deep lesions, such as those formed after major ablative surgery (total and partial removal of breast, melanoma or deep naevi).

Sponges can also be used, like hydrogels, as fillers for bone or dental lesions, optionally combined with pharmacologically and/or biologically active substances, and finally for intra-articular treatment of osteoarthritis and cartilage damage. The addition of collagen to sponges before freeze-drying (which precedes irradiation) again gives them better structural characteristics of stability and elasticity and makes them particularly adaptable to the shape and size of the site at which they will be used.

The derivatives to which this invention relates consist of:
hyaluronic acid;
the specific bifunctional PEG spacer;
a photoreactive, selected from propiophenone and a coumarin derivative which, bonded as described below, form photocrosslinkable intermediates, which in turn, after UV irradiation, give rise to photocrosslinked derivatives in the form of the hydrogels and sponges described and claimed herein. As stated, the derivatives can optionally contain collagen, for the purposes described above.

More specifically, a first object of the present invention is photocrosslinked derivatives of hyaluronic acid (HA) consisting of HA, a bifunctional polyethylene glycol (PEG) spacer which is triethylene glycol, and a photoreactive compound selected from a coumarin derivative and propiophenone.

As stated, the polysaccharide used is hyaluronic acid, the main characteristics of which have already been described. In detail, the HA used herein can derive from any source, such as extraction from rooster combs (EP 138572), fermentation (from *Streptococcus equi* or *zooepidemicus*) or biosynthesis (from *Bacillus*), and have a mean molecular weight ranging between 10 kDa and 1000 kDa, preferably between 40 k Da and 700 kDa, and even more preferably between 160 kDa and 220 kDa; this last fraction will be abbreviated hereafter to "HA with mean MW 200 kDa". It should be emphasised that in the present description, "mean molecular weight" signifies the weight average molecular weight calculated by the "intrinsic viscosity" method (Terbojevich et al., *Carbohydr Res*, 1986, 363-377).

As regards spacers, polyethylene glycol (PEG) is suitable for the purposes of the present invention. PEG is obtained by polymerisation of ethylene oxide; it consists of a linear chain, and is widely used in the chemical and pharmaceutical industry for its versatility, and above all its lack of toxicity. It is also a bifunctional spacer, which can bond to different molecules at each of the two ends of its chain. It can have an extremely variable MW, depending on the degree of polymerisation; for the purposes of the present invention, the PEG used is triethylene glycol, which has a MW of 150 Da; it is therefore a chain substantially formed by three residues.

As regards photoreactives, among the various categories cited, propiophenone and coumarin are successfully used and claimed herein; among the various types of coumarin derivatives available (umbelliferone, aesculetin, scopoletin, psoralens, furanocoumarin and dicoumarol), 7-hydroxy coumarin, also known as umbelliferone, is particularly preferred.

Finally, as regards collagen, native collagen and/or hydrolysed collagen (gelatin) deriving from extraction from all types of tissue, in particular from equine, porcine, bovine and ovine tendon and skin, can be used. In addition to extracted collagens, the various types of collagen produced by biotechnology (fermentative or enzymatic) should not be ruled out. The ratio between photocrosslinkable HA and collagen can range between 5:1 and 1:5 weight/weight, depending on the type of final structure to be obtained; collagen from equine tendon, in a photocrosslinkable HA/collagen ratio ranging between 1:1 and 1:4, is particularly preferred.

A further object of the present invention is the reaction intermediate consisting of the crosslinkable isotonic solution comprising hyaluronic acid (HA), a bifunctional polyethylene glycol (PEG) spacer which is triethylene glycol, and a photoreactive compound selected from a coumarin derivative and propiophenone, wherein the bond between the bifunctional spacer and HA is an ester or amide bond, and the bond between the photoreactive compound and the bifunctional spacer is an ether bond.

The present invention also relates to a medical device containing at least one photocrosslinked derivative of hyaluronic acid according to the present invention.

The present invention also relates to the process for the preparation of derivatives in the form of shape-memory hydrogels, comprising the following steps:

a) formation of an ether bond between PEG and the coumarin derivative or propiophenone;

b) formation of an ester or amide bond between the product obtained at step a) and HA, with a degree of final derivatisation of HA ranging from 5 to 80 mol % in the case of the ester bond, and a degree of final derivatisation of HA ranging from 1 to 50 mol % in the case of the amide bond;

c) solubilisation of the product obtained in step b) and irradiation of the isotonic aqueous solution obtained with UV rays at a wavelength of between 300 and 450 nm, preferably between 320 and 380 nm, for a time of between 1 minute and 24 hours.

The process for the preparation of derivatives according to the present invention in the form of shape-memory sponges comprises the following steps:

a) formation of an ether bond between PEG and the coumarin derivative or propiophenone;

b) formation of an ester or amide bond between the product obtained at step a) and HA, with a final degree of derivatisation of HA ranging from 5 to 80 mol % in the case of the ester bond, and a degree of final derivatisation of HA ranging from 1 to 50 mol % in the case of the amide bond;

b') solubilisation of the product obtained in step b) in isotonic aqueous solution, and freeze-drying of the isotonic aqueous solution thus obtained;

c) irradiation of the product obtained in step b') with UV rays at a wavelength of between 300 and 450 nm, preferably between 320 and 380 nm, for a time of between 1 minute and 24 hours.

The process whereby the gels and sponges according to the present invention are obtained therefore comprises a number of steps, which can be schematically described as follows:

for hydrogels:

a) the photoreactive is bonded to the bifunctional spacer via an ether bond to form a photocrosslinkable group, able to react at a later step with HA;

b) the product obtained in step a) is bonded to HA via an ester or amide bond, which involves the free carboxyl of the glucuronic acid residue; the final degree of derivatisation of HA ranges between 5 and 80 mol % for the ester bond, and between 1 and 50 mol % for the amide bond. The resulting precipitate is soluble in water and/or aqueous solution and sterilisable after solubilisation by filtration through an 0.22 µm filter;

c) the product obtained in step b) is dissolved in isotonic aqueous solution and irradiated with UV rays at a wavelength of between 300 and 450 nm, preferably between 320 and 380 nm, for between 1 minute and 24 hours, and the resulting substance is the final photocrosslinked product;

for sponges:

b) the product obtained in step a) is bonded to HA via an ester or amide bond, which involves the free carboxyl of the glucuronic acid residue; the final degree of derivatisation of HA ranges between 5 and 80 mol % for the ester bond, and between 1 and 50 mol % for the amide bond;

b') the product obtained in the preceding step b) is dissolved in isotonic aqueous solution, and the resulting solution is subjected to the freeze-drying process, which consists of three separate steps: freezing; sublimation (or primary drying); and desorption (or secondary drying);

c) the lyophilisate thus obtained is irradiated with UV rays at a wavelength of between 300 and 450 nm, preferably between 320 and 380 nm, for between 1 minute and 24 hours;

The most complex step of the entire process is naturally step b), because the bond between HA and the spacer-photoreactive can be the ester or amide type, therefore involving different functions and requiring different conditions; the resulting gels and sponges will have different characteristics, depending on the nature of the bond.

In detail, the Applicant presents a schematic illustration of step b), in relation to the type of bond to be created:

Preparation of an Ester Derivative (A) of HA and Photocrosslinkable Group

- Preparation of a quaternary ammonium salt of HA, from HA sodium salt having a molecular weight ranging between 40 kDa and 700 kDa, preferably between 160 and 220 kDa.
- Reaction of the quaternary ammonium salt of HA in polar aprotic solvent (DMSO, DMF or NMP, preferably DMSO), at the concentration of 1 to 200 mg/mL, with halide derivatives (iodides, bromides or chlorides, preferably iodides) of suitably prepared photocrosslinkable groups, and in a halide/HA molar ratio ranging between 0.05 and 0.8, preferably between 0.2 and 0.5, at a T ranging between 20° C. and 50° C., more preferably between 35° and 45° C., for a time ranging between 4 h and 72 h, preferably between 18 h and 48 h.
- Isolation and purification of HA derivative (A) esterified with photocrosslinkable groups and in the form of sodium salt by precipitation and washing in organic solvent (ethanol, ethyl acetate, acetone); the final degree of derivatisation of HA ranges between 5 and 80 mol %:

Preparation of an Amide Derivative (B) of HA and Photocrosslinkable Group

- Preparation of an HA quaternary ammonium salt from HA sodium salt having a molecular weight ranging between 40 kDa and 700 kDa, preferably between 160 and 220 kDa.
- Activation of the HA quaternary ammonium salt in polar aprotic solvent (DMSO, DMF or NMP, preferably DMSO) with an activating agent (CDI, CMPJ, EDC, HOBT or NHS, preferably CDI), with an activating agent/HA molar ratio ranging between 0.01 and 0.5, for a time ranging between 0.1 h and 3 h, at a T ranging between 35° C. and 45° C.
- Reaction of HA activated with amine derivatives of photocrosslinkable groups suitably prepared in polar aprotic solvent (DMSO, DMF or NMP, preferably DMSO) in an amine/HA molar ratio ranging between 0.01 and 1.5, at a T ranging between 35 and 45° C., for a time ranging between 4 h and 30 h (preferably between 12 h and 24 h). The degree of final derivatisation of HA ranges between 1 and 50 mol %.
- Isolation and purification of HA derivative (B) amidated with photocrosslinkable groups and in the form of a sodium salt by precipitation and washing in organic solvent (ethanol, ethyl acetate, acetone).

As regards hydrogels and sponges, the steps of the corresponding production processes are shown schematically below:

Preparation of a Hydrogel Based on HA Derivative (A) Esterified with Photocrosslinkable Groups:

- Preparation of an isotonic aqueous solution of (A) in phosphate, acetate or saline buffer (preferably saline), at a concentration ranging between 5 and 70 mg/ml
- Sterilisation by filtration through 0.22 μm cellulose acetate filters
- Housing of the sterile solution in containers transparent to UV rays (such as polyethylene)
- Irradiation of the solution with a Wood's lamp and a beam of light at a wavelength ranging between 300 and 450 nm, more preferably between 320 a 380 nm, for a time ranging between 1 minute and 24 h;

Preparation of a Hydrogel Based on HA Derivative (B) Amidated with Photocrosslinkable Groups

- Preparation of an isotonic aqueous solution of (B) in phosphate, acetate or saline buffer (preferably phosphate buffer) at a concentration ranging between 1 and 40 mg/mL
- Sterilisation by autowashing or filtration through 0.22 μm cellulose acetate filters
- Housing of the sterile solution in containers transparent to UV rays (such as polyethylene)
- Irradiation of the solution with a Wood's lamp and a beam of light at a wavelength ranging between 300 and 370 nm, more preferably between 320 a 365 nm, for a time ranging between 1 minute and 24 h;

Preparation of a Sponge:

- Preparation of an isotonic aqueous solution (containing 0.9% NaCl, or mannitol ranging from 1 to 20% weight/volume, or isopropanol ranging from 1 to 20% volume/volume, or glucose ranging from 1 to 20% weight/volume), preferably only water, of an ester or amide HA derivative with a photocrosslinkable group at a concentration ranging between 1 and 70 mg/ml.
- Freeze-drying in the following steps:
  freezing: the solution is poured into suitable trays (to give a thickness of between 0.5 and 20 mm, preferably between 2 and 7 mm) resting on the freeze-dryer plates, and the cooling T of the plates is set to −3° C. and maintained at that temperature until the solution reaches 2° C. (between 1 and 8 hours, preferably between 4 and 5 hours). The T of the plates is reduced to −30° C., and maintained as long as required for the solution to reach a T of at least −20° C. (between 3 and 10 hours, preferably between 4 and 7 hours);
  sublimation (or primary drying): the condenser of the apparatus is adjusted to a T of at least −30° C., and with the vacuum pump, the pressure in the freeze-dryer chamber is reduced to a value ranging between $8 \times 10^{-1}$ and $5 \times 10^{-3}$ mbar, preferably between $8 \times 10^{-2}$ and $2 \times 10^{-2}$ mbar. The plates are then heated gradually (in a time ranging between 1 and 3 hours) to a T of between −10° and 10° C., preferably 0° C.; the T is kept stable for at least 12 hours, or until the product reaches the same T as the plates, pressure being equal;
  desorption (or secondary drying): the plates are heated gradually (in a time ranging between 1 and 3 hours) to a T of between 15° and 55° C., preferably 25° C., without varying the pressure applied. The T is kept stable for at least 8 hours, or until the product reaches the same T as the plates. After ensuring that desorption is complete, the pressure is restored in the freeze-dryer chamber by injecting dehydrated, microfiltered nitrogen;
- Irradiation of the freeze-dried solid obtained from the preceding step with a beam of light having a wavelength ranging between 300 and 450 nm, preferably between 320 and 380 nm, for a time of between 1 minute and 24 h.

For sponges, as for hydrogels, the duration of irradiation is very variable, being strongly influenced by the selectivity of the wavelength, the intensity of the emission of the UV lamp, the thickness of the material and the irradiation procedures. The latter vary according to the type of lamp used; if a single lamp is used, the sample is rotated so that its entire surface is exposed to the UV rays. Rotation is not required if a multilamp is used, as it simultaneously irradiates the whole exposed surface. It should also be noted that by modulating the parameters involved (concentration of initial solution, type of solvent used, freeze-drying conditions and irradiation conditions), the degree of porosity of the sponges and compactness of the hydrogel can be established a priori. This aspect is of crucial importance bearing in mind that sponges in particular, but also hydrogels, are colonisable by cells. The cells, whether differentiated or undifferentiated, can be inserted in the sponge or hydrogel before implantation and suitably cultured; alternatively, the sponge or hydrogel can be implanted in the lesion to be treated, allowing it to be colonised by the cells physiologically present in the site of the lesion.

As stated, the Applicant has surprisingly discovered that the specific characteristics of the hydrogels and sponges claimed herein depend to a crucial extent on the length of the chain of the spacer used (PEG), as well as on its chemical nature. It has been demonstrated by means of numerous tests that spacers with long chains prevent homogenous, compact gelling of the material, which is no longer definable as "shape-memory"; a similar result is obtained by eliminating the spacer. These characteristics are also found in sponges, which become very fragile and totally incapable of maintaining their shape not only after being soaked and squeezed, but also after being simply placed in aqueous solution. In particular, the Applicant has unexpectedly found that a PEG chain consisting of three residues gives the materials described herein the characteristics already discussed. In view of all these factors, the Applicant has also synthesised some similar photocrosslinkable derivatives without spacers, to compare the resulting products.

Some preparation examples of the hydrogels and sponges described and claimed herein are set out below according to the processes illustrated.

The photoreactives used are 7-hydroxycoumarin (umbelliferone) or propiophenone, which must be suitably treated so that they bond to the bifunctional spacer (triethylene glycol) or react directly with HA, to give the comparison products. The examples follow the scheme set out below:

Examples 1, 2 and 3: umbelliferone-triethylene glycol to be bonded to HA via an ester bond;
Example 4: umbelliferone derivatised to bond to HA with an ester bond (direct);
Examples 5 and 6: umbelliferone-triethylene glycol to be bonded to HA via an amide bond;
Examples 7 and 8: propiophenone-triethylene glycol to be bonded to HA with an ester bond (indirect).

Example 1: Synthesis of 2-(2-(2-chloroethoxyl)ethoxy)ethyl 4-methylbenzenesulphonate (1)

180 mL of anhydrous CH$_2$Cl$_2$, 10.0 mL of (2-(2-(2-chloroethoxyl)ethoxy)ethanol, 10.55 mL of triethylamine (Et$_3$N) and 16.8 g of N,N'dimethylaminopyridine (DMAP) are introduced into a two-necked flask equipped with magnetic stirring, argon flow and ice bath. 14.43 g of tosyl chloride (TsCl), dissolved in 60 mL of anhydrous CH$_2$Cl$_2$, is then added, maintaining the T at 0° C. under argon flow. The reaction is left to proceed at 0° C. for 1 h 30 min, and then at room temperature for 3 h 30 min. The organic phase is washed with water, 1N HCl, saturated aqueous NaHCO$_3$ and saturated aqueous NaCl and dried on MgSO$_4$, and the solvent is then removed at low pressure. $^1$H NMR analysis detects the presence of the desired product, which requires no further purification.

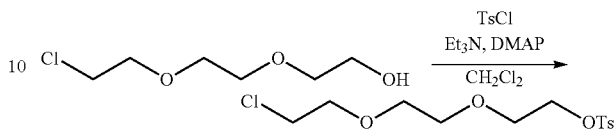

Example 2: Synthesis of 7-(2-(2-(2-chloroethoxyl)ethoxy)ethoxy)-2H-chromen-2-one (2)

18.3 g of umbelliferone, 200 mL of acetone, and 39.0 g of 2-(2-(2-chloroethoxyl)ethoxy)ethyl 4-methylbenzenesulphonate (1), taken up with acetone (600 mL), 93.6 g of K$_2$CO$_3$ and 18-crown-6 in catalytic amount, are introduced into a two-necked flask equipped with magnetic stirring, oil bath, coolant and argon flow. The reaction is left to proceed to reflux under stirring for 24 h; the cooled reaction mixture is then filtered through a Gooch funnel with celite, and the solvent is removed at low pressure. The nature of the product obtained is confirmed by $^1$H NMR analysis (white crystalline solid).

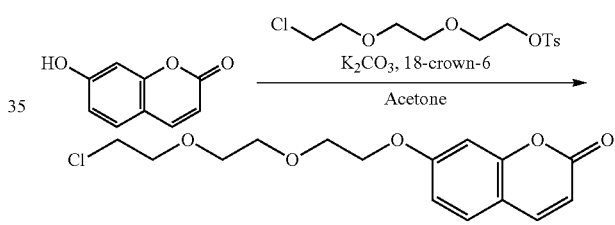

Example 3: Synthesis of 7-(2-(2-(2-iodoethoxy)ethoxy)ethoxy)-2H-chromen-2-one (3)

2.5 g of 7-(2-(2-(2-chloroethoxy)ethoxy)ethoxy)-2H-chromen-2-one (2) and acetone (50 mL) are introduced into a two-necked flask equipped with magnetic stirring, oil bath and coolant. Sodium iodide (8.35 g) is then added, and the mixture is left to proceed to reflux under stirring for 48 h. The work-up is performed by leaving the mixture to cool, filtering it through a Gooch funnel and celite, and then removing the solvent at low pressure. The nature of the end product is confirmed by the $^1$H NMR spectroscopic analysis (white crystalline solid) reported in FIG. 1.

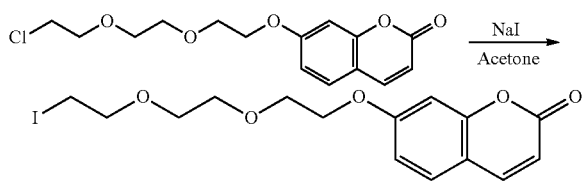

In FIG. 1: $^1$H NMR of (3) in CDCl$_3$, 400 MHz, δ (ppm): 7.63 (d, J=9.5 Hz, 1H), 7.37 (d, J=8.6 Hz, 1H), 6.89-6.84 (m, 2H), 6.26 (d, J=9.5 Hz, 1H), 4.24-4.15 (m, 2H), 3.95-3.88 (m, 2H), 3.80-3.66 (m, 6H), 3.26 (t, J=6.9 Hz, 2H).

Example 4: Synthesis of 7-bromomethyl coumarin (4)

7-Methylcoumarin (3.0 g), N-bromosuccinimide (3.34 g) and carbon tetrachloride (80 mL) are introduced into a two-necked flask equipped with oil bath, magnetic stirring and coolant. AIBN (31 mg) is introduced under stirring, and the mixture is left to proceed to reflux (106° C.) under stirring for 1 h 30 min. The mixture is cooled to room temperature, the solvent is removed with a rotary evaporator and mechanical pump; the residue is then taken up with water, and the reaction is left to proceed for 2 h under stirring. The mixture is filtered through a Gooch funnel, and the precipitate is taken up with water and left to proceed under stirring for a further hour. The mixture is filtered through a Gooch funnel, and the solvent is then removed with a mechanical pump. The desired product is obtained, and its nature is confirmed by $^1$H NMR analysis.

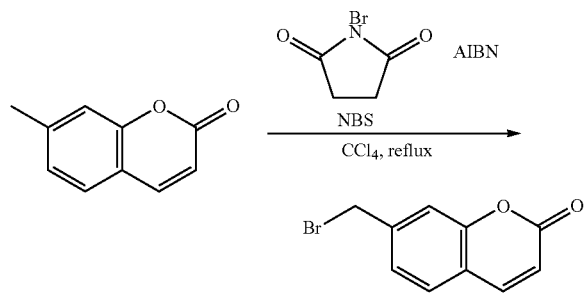

Example 5: Synthesis of 7-(2-(2-(2-azidoethoxy) ethoxy)ethoxy)-2H-chromen-2-one (5)

4.0 g of 7-(2-(2-(2-iodoethoxy)ethoxy)ethoxy)-2H-chromen-2-one (3) (obtained as described in example 3), 1.93 g of NaN$_3$ and 30 mL of distilled water are introduced into a two-necked flask equipped with magnetic stirring, oil bath and coolant. The reaction is left to proceed to reflux under stirring overnight, and then extracted with CH$_2$Cl$_2$, dried on MgSO$_4$ and filtered through a Gooch funnel. The solvent is removed at low pressure. The product is purified by flash chromatography (eluent cyclohexane/AcOEt 2:1). A pale yellow transparent oil is obtained, the nature of which is confirmed by $^1$H NMR analysis.

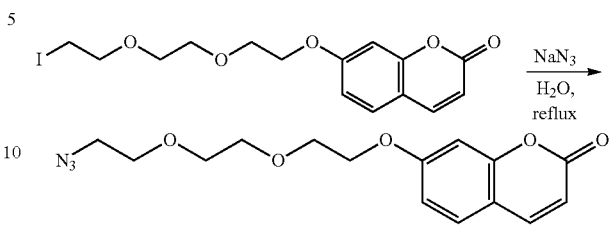

Example 6: Synthesis of 7-(2-(2-(2-aminoethoxy) ethoxy)ethoxy)-2H-chromen-2-one (6)

Figure 2:
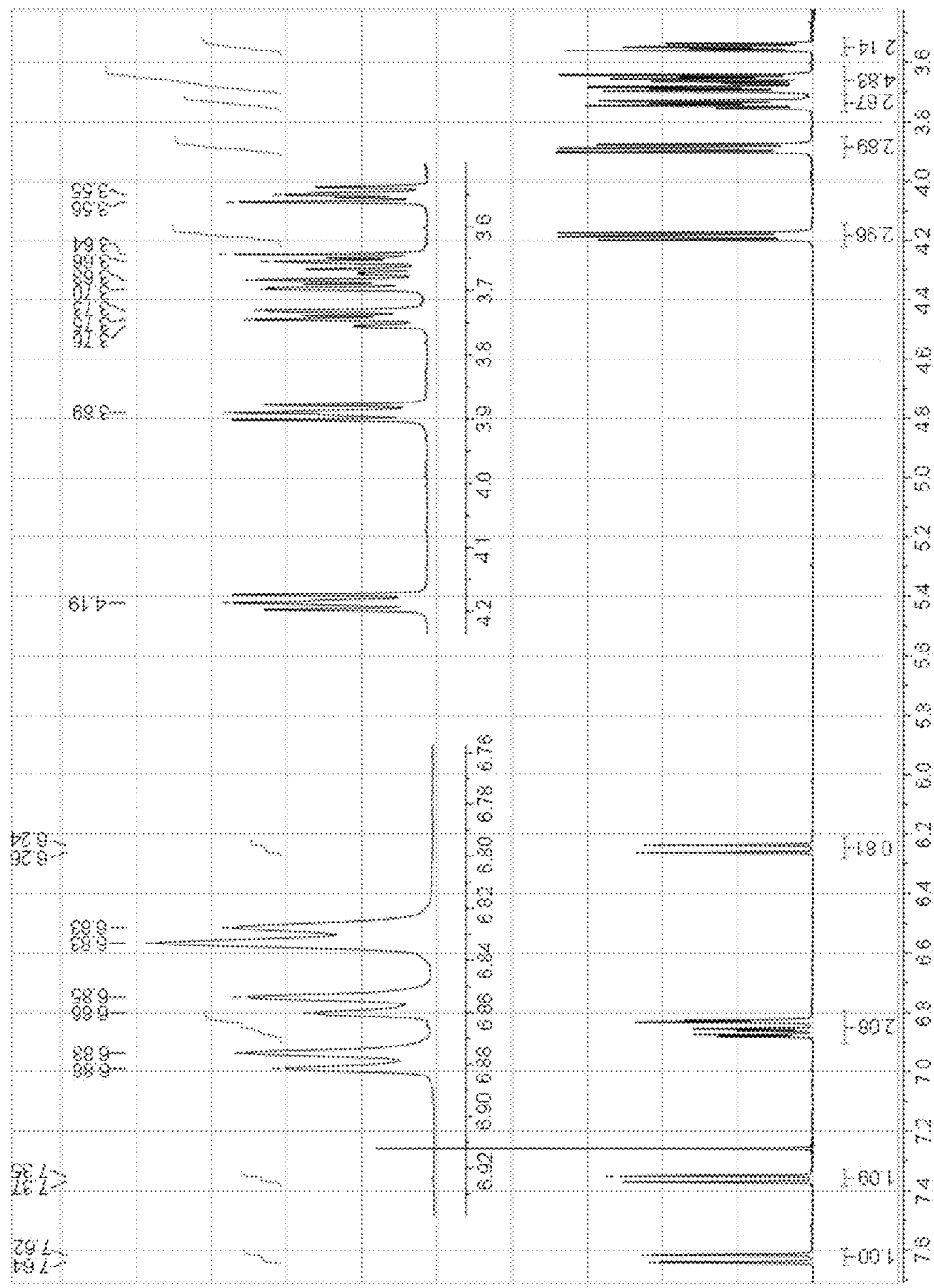
FIG. 2 shows the $^1$-NMR spectrum of 7-(2-(2-(2-aminoethoxy)ethoxy)ethoxy)-2H-chromen-2-one (Example 6) in $CDCl_3$.

2.02 g of 7-(2-(2-(2-azidoethoxy)ethoxy)ethoxy)-2H-chromen-2-one (5) is dissolved in 25 mL of anhydrous THF in a two-necked flask equipped with magnetic stirring, ice bath and argon flow. At 0° C. 1,742 g of triphenylphosphine is introduced, and the reaction is left to stand at room temperature, always under stirring, for 18 h. 3 mL of distilled H$_2$O is introduced, and the reaction is left to proceed under stirring overnight at room temperature. The solvent is removed at low pressure, and the product is then purified by flash chromatography. The nature of the product obtained is confirmed by $^1$H NMR analysis. The $^1$H-NMR spectrum of (6) in CDCl$_3$ is shown in FIG. 2.

Example 7: Synthesis of 1-(4-(2-(2-(2-(2-chloroethoxy)ethoxy) ethoxy)ethoxy)phenyl)-2-hydroxy-2-methylpropan-1-one (7)

31.2 g of 2-hydroxy-1-(4-(2-hydroxyethoxy)phenyl)-2-methylpropan-1-one, 400 mL of acetone, and 39.0 g of 2-(2-(2-chloroethoxyl)ethoxy)ethyl 4-methylbenzenesulphonate, synthesised as reported in example 1, and taken up with acetone (600 mL), 93.6 g of K$_2$CO$_3$ and 18-crown-6 in catalytic amount are introduced into a two-necked flask equipped with mechanical stirring, oil bath, coolant and argon flow. The reaction is left to proceed to reflux under stirring for 24 h; the cooled reaction mixture is then filtered through a Gooch funnel with celite, and the solvent is removed at low pressure. The nature of the product obtained is confirmed by $^1$H NMR analysis (white crystalline solid).

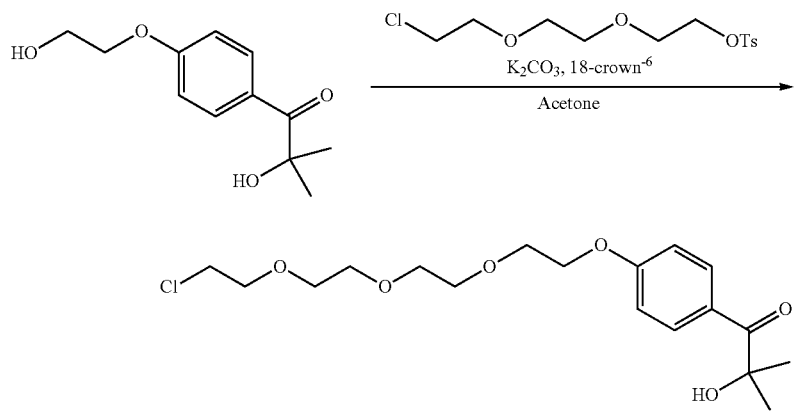

Example 8: Synthesis of 2-hydroxy-1-(4-(2-(2-(2-(2-iodoethoxy)ethoxy)ethoxy)ethoxy)phenyl)-2-methylpropan-1-one (8)

Figure 3:
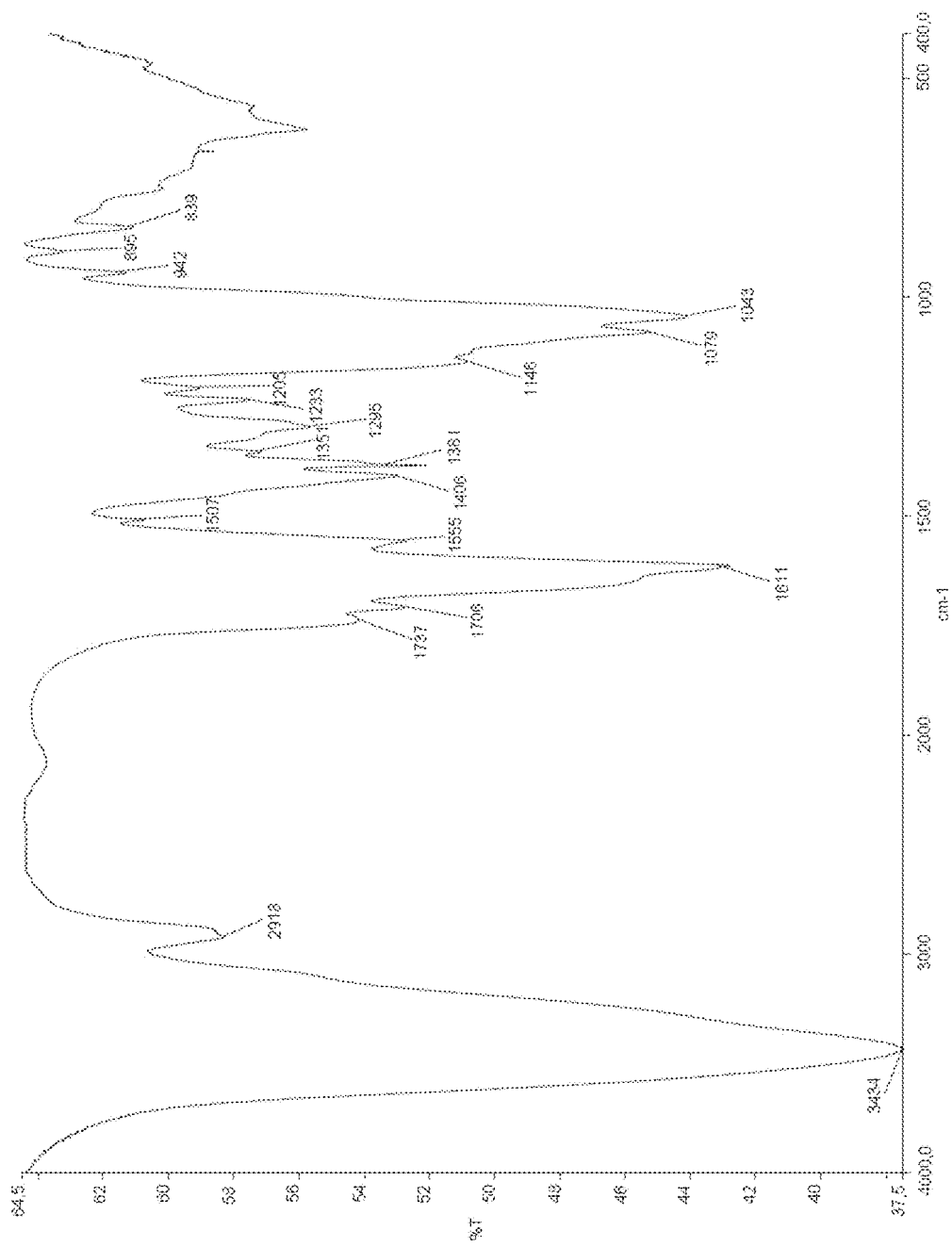
FIG. 3 shows the FTIR spectrum of an HA ester derivative with 7-(2-(2-(2-iodoethoxy)ethoxy)ethoxy)-2H-chromen-2-one (Example 9).
Figure 4:
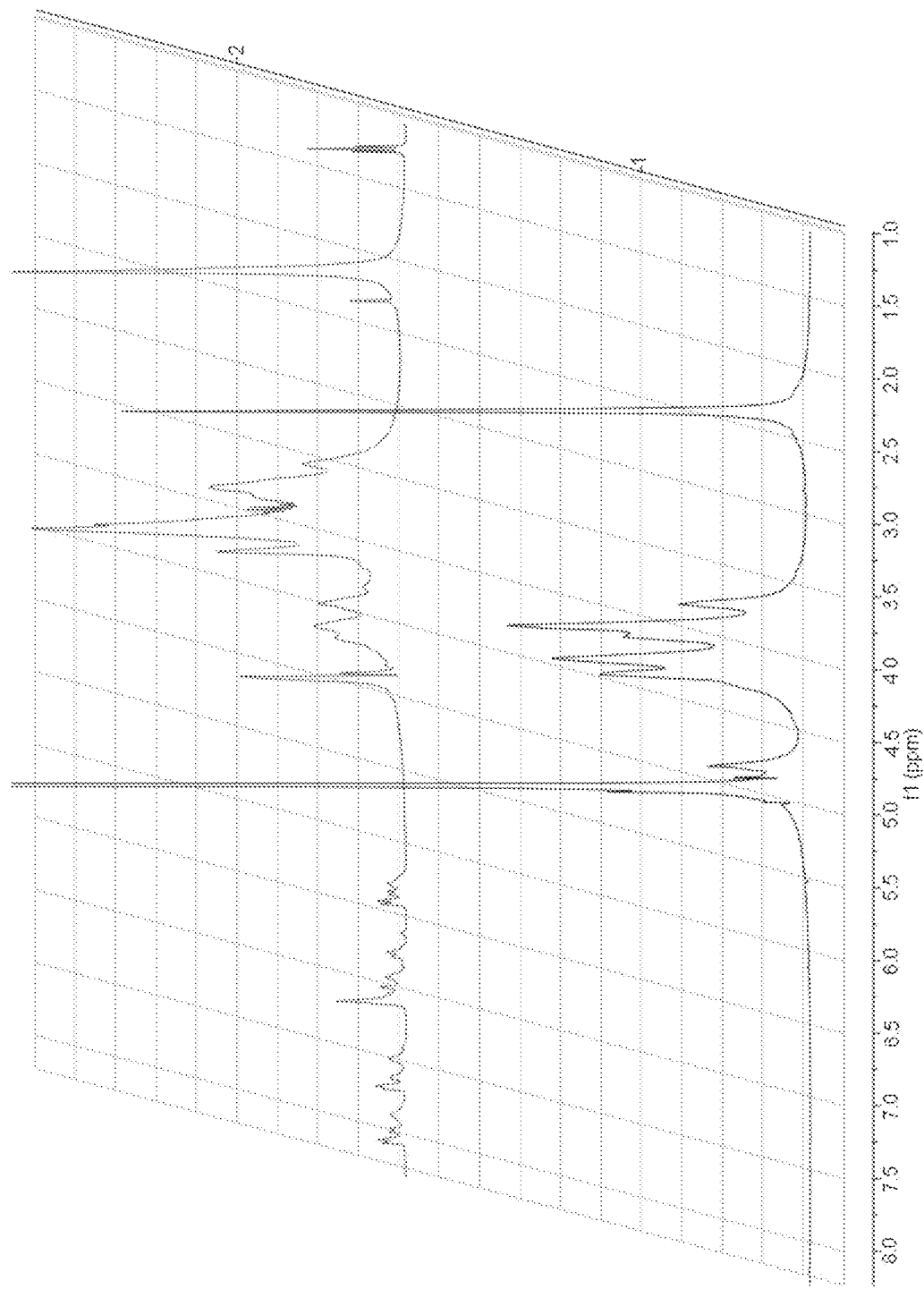
FIG. 4 shows the $^1$-NMR spectrum of an HA ester derivative with 7-(2-(2-(2-iodoethoxy)ethoxy)ethoxy)-2H-chromen-2-one (Example 9) (line A) compared with HANa (line B) in $D_2O$.

4.0 g of 1-(4-(2-(2-(2-(2-chloroethoxy)ethoxy)ethoxy)ethoxy)phenyl)-2-hydroxy-2-methylpropan-1-one (7) and acetone (80 mL) are introduced into a two-necked flask equipped with magnetic stirring, oil bath and coolant. Sodium iodide (8.35 g) is then added, and the mixture is left to proceed to reflux under stirring for 48 h. The work-up is performed by leaving the mixture to cool, filtering it through a Gooch funnel and celite, and then removing the solvent at low pressure. The nature of the end product is confirmed by $^1$H NMR spectroscopic analysis (white crystalline solid).

analysed by FTIR, RP-HPLC and $^1$H-NMR, exhibiting a functionalisation of 32% and a yield of 92%. FIG. 3 shows the FTIR spectrum of (9), and FIG. 4 shows the $^1$H-NMR spectrum of (9) (line A) compared with HANa (line B) in $D_2O$.

Example 10: Synthesis of an HA Ester Derivative with 7-(2-(2-(2-iodoethoxy)ethoxy)ethoxy)-2H-chromen-2-one (10)—Final Functionalisation 50%

In a glass reactor equipped with a thermostatable glycol jacket and magnetic stirring, 2.0 g of HATBA is dissolved in 240 mL of anhydrous DMSO, and 521 mg of 7-(2-(2-(2-iodoethoxy)ethoxy)ethoxy)-2H-chromen-2-one (1.0241 g),

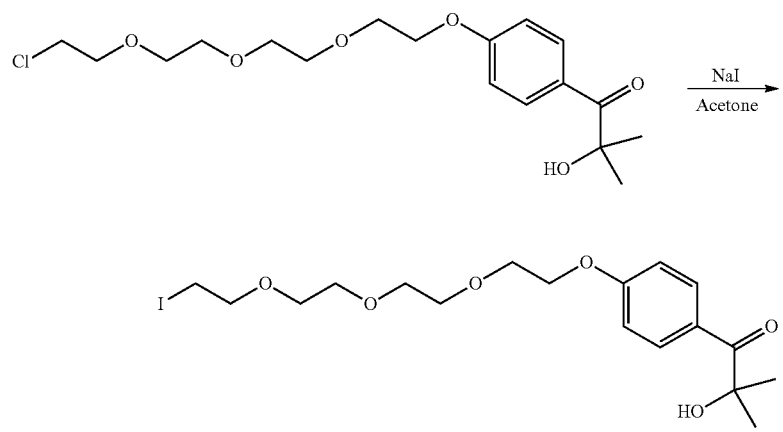

The photoreactives obtained as described above were reacted with HA as follows:
- Examples 9 and 10: umbelliferone-triethylene glycol bonded to HA via ester;
- Examples 11 and 12: umbelliferone bonded to HA via ester;
- Examples 13 and 14: umbelliferone-triethylene glycol bonded to HA via amide;
- Example 15: propiophenone-triethylene glycol bonded to HA via ester.

Example 9: Synthesis of an HA Ester Derivative with 7-(2-(2-(2-iodoethoxy)ethoxy)ethoxy)-2H-chromen-2-one (9)—Final Functionalisation 30%

In a glass reactor equipped with a thermostatable glycol jacket and magnetic stirring, 2.0 g of HATBA is dissolved in 240 mL of anhydrous DMSO, and 521 mg of 7-(2-(2-(2-iodoethoxy)ethoxy)ethoxy)-2H-chromen-2-one (3) (521 mg), prepared as reported in example 3, is added. The reaction proceeds for 48 h at 40° C.; a saturated solution of NaBr is then added under stirring, and precipitation is effected by adding EtOH drop by drop. The product is purified by washing in EtOH/H$_2$O 95:5 and absolute EtOH, then dried under high vacuum. The product thus obtained is prepared as reported in example 3, is added. The reaction proceeds for 48 h at 40° C.; a saturated solution of NaBr is then added under stirring, and precipitation is effected by adding EtOH drop by drop. The product is purified by washing in EtOH/H$_2$O 95:5 and absolute EtOH, then dried under high vacuum. The product thus obtained is analysed by FTIR, RP-HPLC and $^1$H-NMR, demonstrating a functionalisation of 49% and a yield of 86%.

Example 11: Synthesis of an HA Ester Derivative with 7-(bromomethyl)-2H-chromen-2-one (11)—Final Functionalisation 40%

2.0 g of HATBA is dissolved in 240 mL of DMSO in a glass reactor, equipped with thermostatable glycol jacket and magnetic stirring. 308 g of 7-bromomethyl-2H-chromen-2-one (4), prepared as reported in example 4, is then added, and the reaction is left to proceed for 72 h at 40° C. A saturated solution of NaBr is added under stirring, followed by precipitation with 96% EtOH. The product is purified by washing in 96% EtOH/H$_2$O 8:2 and absolute EtOH. A powdery white compound is obtained, which is left to dry under high vacuum.

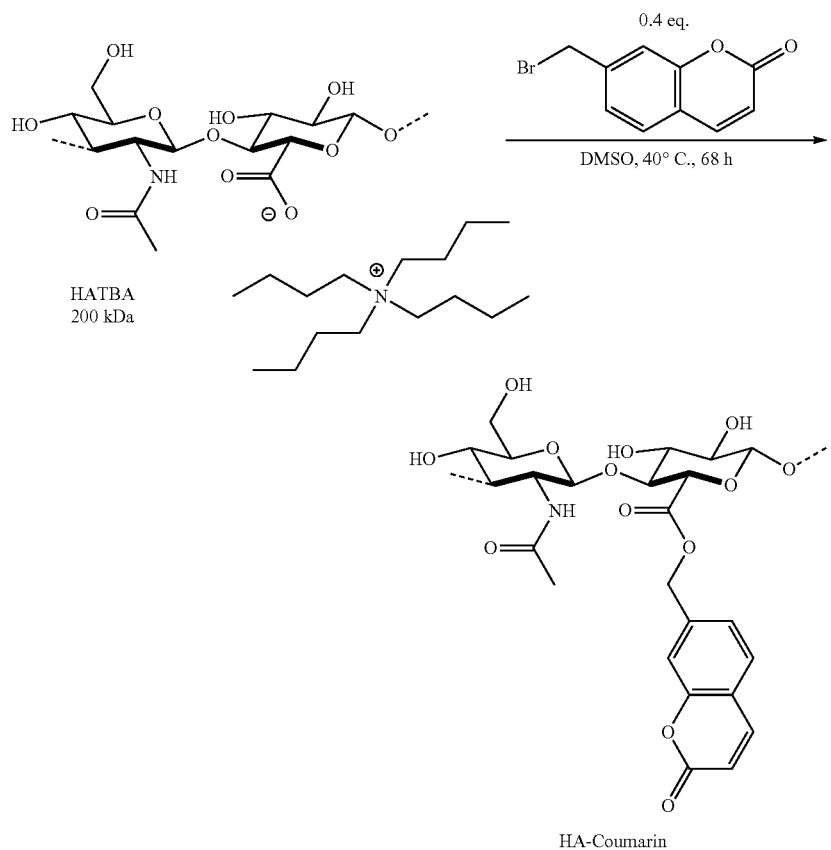

Example 12: Synthesis of an HA Ester Derivative with 7-(bromomethyl)-2H-chromen-2-one (12)—Final Functionalisation 90%

Figure 5:
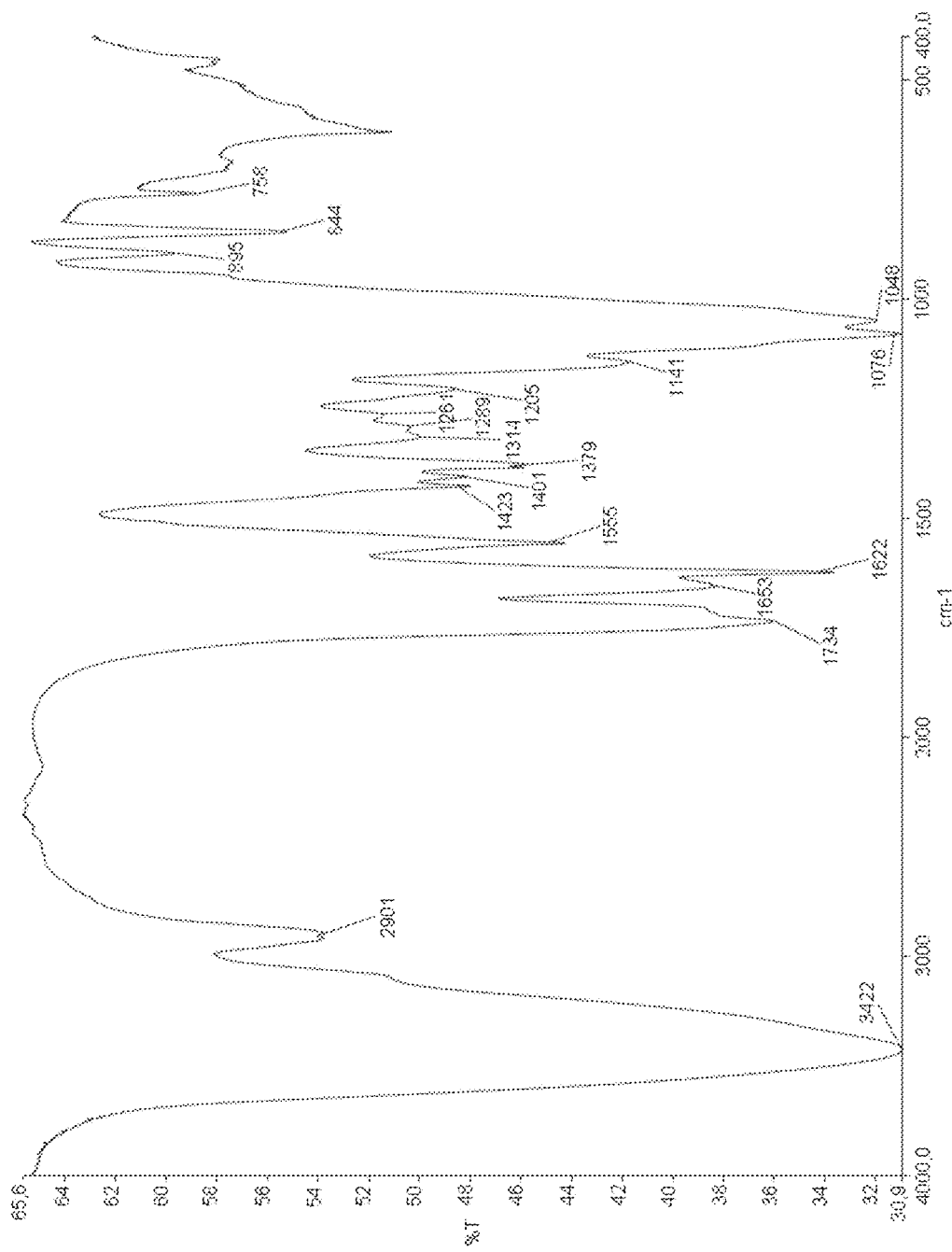
FIG. 5 shows FTIR spectrum of 2-hydroxy-1-(4-(2-(2-(2-iodoethoxy)ethoxy)ethoxy)phenyl)-2-methylpropan-1-one (Example 8).

2.0 g of HATBA is dissolved in 240 mL of DMSO in a glass reactor, equipped with thermostatable glycol jacket and magnetic stirring. 1.011 g of 7-bromomethyl-2H-chromen-2-one (4), prepared as reported in example 4, is then added, and the reaction is left to proceed for 72 h at 40° C. A saturated solution of NaBr is added under stirring, followed by precipitation with 96% EtOH. The product is purified by washing in 96% EtOH/H$_2$O 8:2 and absolute EtOH. A powdery white compound is obtained, which is left to dry under high vacuum. The product is analysed by FTIR, RP-HPLC and $^1$H-NMR, demonstrating a functionalisation of 91%. The FTIR spectrum of (8) is shown in FIG. 5.

Example 13: Synthesis of an HA Amide Derivative with 7-(2-(2-(2-aminoethoxy)ethoxy)ethoxy)-2H-chromen-2-one (13)—Final Functionalisation 20%

2.0 g of HATBA is dissolved in 200 mL of DMSO in a glass reactor, equipped with thermostatable glycol jacket and magnetic stirring. 63 µl of methanesulphonic acid and 0.1145 g of carbonyl diimidazole are then added, and the reaction is left to proceed for 1 h at 42° C. 0.7208 g of 7-(2-(2-(2-aminoethoxy)ethoxy)ethoxy)-2H-chromen-2-one (6), prepared as reported in example 6, is then added, and left under stirring at 40° C. for 24 h. A saturated solution of NaBr is added under stirring, followed by precipitation with 96% EtOH. The product is purified by washing in 96% EtOH/H$_2$O 8:2 and absolute EtOH. A powdery white compound is obtained, which is left to dry under high vacuum.

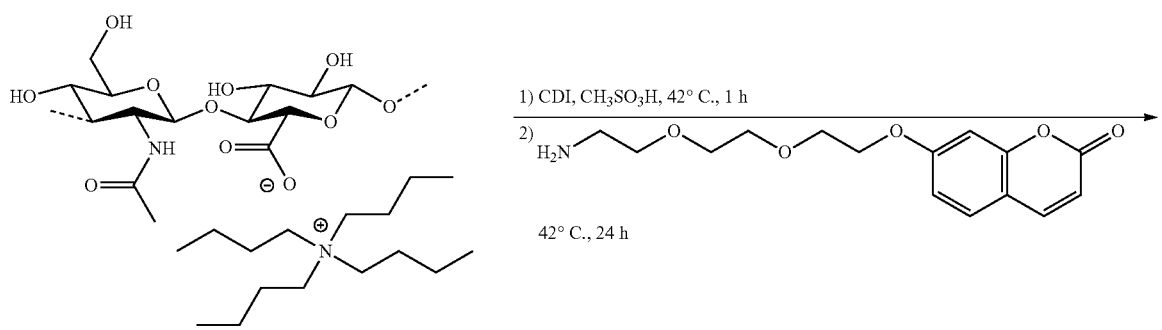

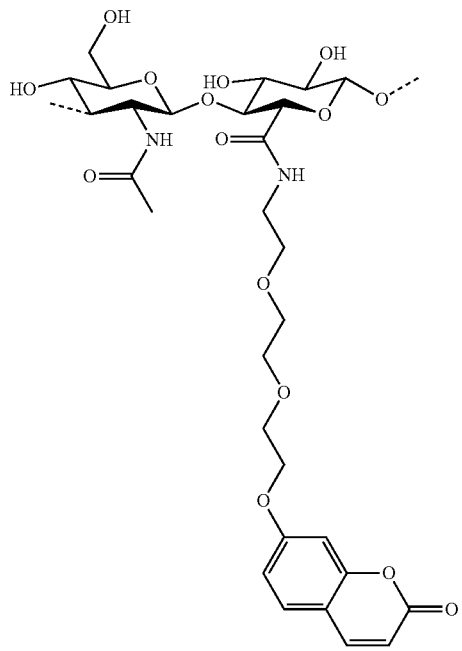

Example 14: Synthesis of an HA Amide Derivative with 7-(2-(2-(2-aminoethoxy)ethoxy)ethoxy)-2H-chromen-2-one (14)—Final Functionalisation 40%

2.0 g of HATBA is dissolved in 200 mL of DMSO in a glass reactor, equipped with thermostatable glycol jacket and magnetic stirring. 63 µl of methanesulphonic acid and 0.2389 g of carbonyl diimidazole are then added, and the reaction is left to proceed for 1 h at 42° C. 1.4015 g of 7-(2-(2-(2-aminoethoxy)ethoxy)ethoxy)-2H-chromen-2-one (6), obtained as reported in example 6, is then added, and the reaction is left to proceed under stirring at 40° C. for 24 h. A saturated solution of NaBr is then added under stirring, followed by precipitation with 96% EtOH. The product is purified by washing in 96% EtOH/H$_2$O 8:2 and absolute EtOH. A powdery white compound is obtained, which is left to dry under high vacuum.

Example 15: Synthesis of an HA Ester Derivative with 2-hydroxy-1-(4-(2-(2-(2-(2-iodoethoxy)ethoxy)ethoxy)ethoxy)phenyl)-2-methylpropan-1-one (15)—Final Functionalisation 50%

In a glass reactor equipped with a thermostatable glycol jacket and magnetic stirring, 2.0 g of HATBA is dissolved in 240 mL of anhydrous DMSO, and 751 mg of 2-hydroxy-1-(4-(2-(2-(2-(2-iodoethoxy)ethoxy)ethoxy)ethoxy)phenyl)-2-methylpropan-1-one (8), prepared as reported in example 8, is added. The reaction proceeds for 48 h at 40° C.; a saturated solution of NaBr is then added under stirring, and precipitation is effected by adding EtOH drop by drop. The product is purified by washing in EtOH/H$_2$O 95:5 and absolute EtOH, then dried under high vacuum. The product thus obtained is analysed by RP-HPLC and $^1$H-NMR, demonstrating a functionalisation of 45% and a yield of 89%.

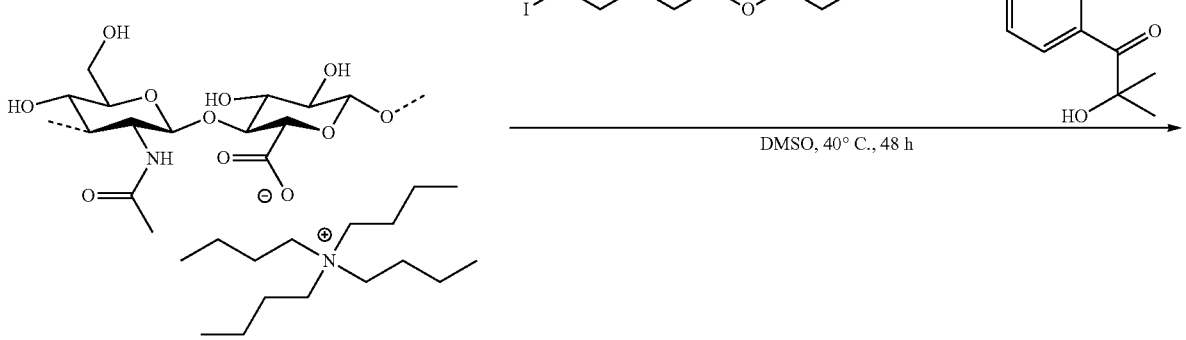

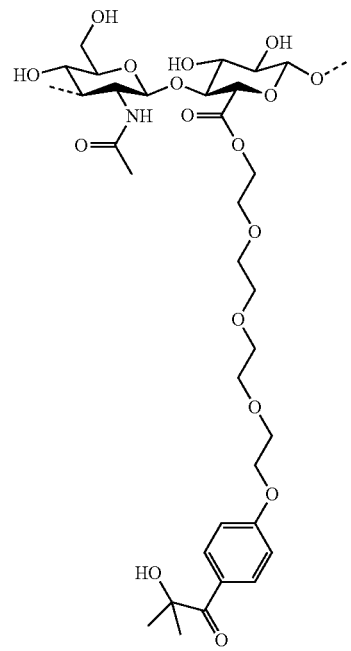

The compounds obtained according to the processes described above were tested for solubility and filterability on a sterile filter, as described in the following Example 16: Test of Solubilisation and Subsequent Gelling of the Compounds Prepared as Described in Examples 9 and 11

Figure 6:
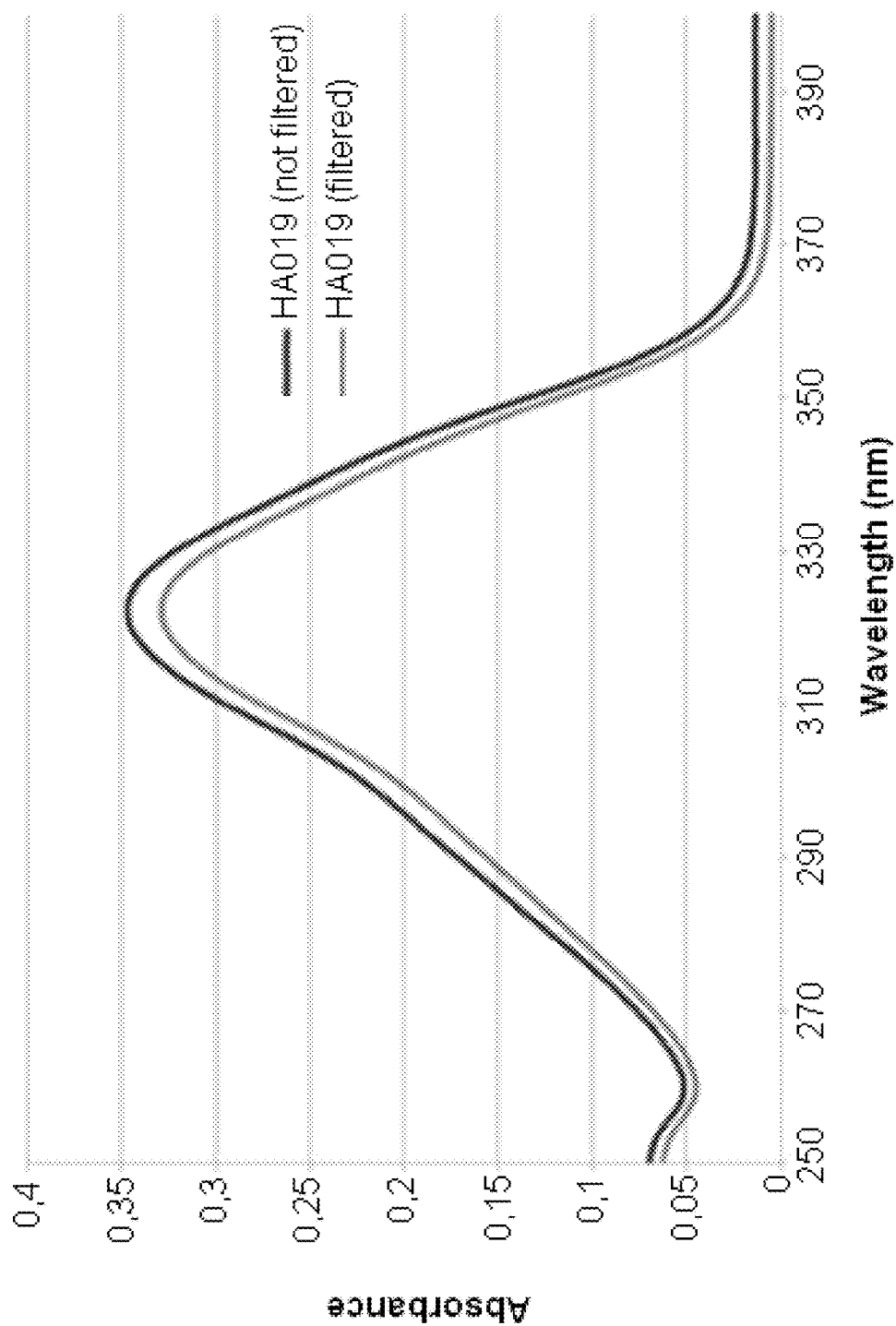
FIG. 6 shows the UV spectrum of a solution of 7-(2-(2-(2-iodoethoxy)ethoxy)ethoxy)-2H-chromen-2-one (Example 9), called HA019, at the concentration of 30 mg/mL, before and after filtration through 0.22 µm RC.

Solutions with a known concentration ranging from 10 to 40 mg/mL were prepared by dissolving the products obtained by the syntheses reported in examples 9 and 11 in aqueous solvent (saline solution 0.9% NaCl, phosphate buffer, etc.). The solutions thus obtained appear clear, and not very viscous; to evaluate the possibility of filtration through 0.2 μm regenerated cellulose (RC) sterilising filters, the UV spectra of the solutions were recorded before and after filtration, comparing the absorbances at 320 nm. The values recorded indicate that the product can be filtered in this way with 97% recovery. FIG. 6 shows the UV spectrum of a solution of (9), called HA019, at the concentration of 30 mg/mL, before and after filtration through 0.22 μm RC.

This aspect is of crucial importance, as a solution filtratable through a sterile filter can be sterilised before moving on to the next steps of the process, and consequently freed of all impurities. Moreover, loss of product at the sterilisation step is minimal, so the process described is definitely economical from the industrial standpoint.

The gelling tests were performed on the same products (as described in Examples 9 and 11), previously dissolved in saline solution at a concentration ranging between 10 and 40 mg/mL. After being filtered through 0.2 μm filters, the solutions are placed in containers and irradiated for a time t ranging between 1 and 20 minutes, with a beam of light having a wavelength of 300-380 nm at room temperature or at 37° C. (there are no significant variations). In the case of the product obtained as described in example 9, a hydrogel forms at all the concentrations tested; the greater the concentration of the starting solution or the irradiation time, the greater the compactness. The product obtained as described in example 11, including after lengthy irradiation of solutions at different concentrations, does not produce a hydrogel of the same consistency as product (9).

In particular, product (9) has a compact shape-memory structure even at the concentration of 10 mg/mL, after only 5 minutes' irradiation. As stated, the compactness of the gel increases with irradiation time, concentration being equal, so that at the concentration of 30 mg/mL after only 5 minutes' irradiation, and even more after 10, 15 or 20 minutes, extremely compact hydrogels form which can withstand cutting, pressures and manipulations without any alternation in their structure.

Conversely, product (11), at the concentration of 30 mg/mL, only reaches a modest degree of compactness after 15 minutes' irradiation; after 5 and 10 minutes the gel is unable to maintain the shape of the container, still less to withstand compression or cutting.

It is therefore evident that the hydrogel obtained by irradiation of a solution of umbelliferone bonded to triethylene glycol and subsequently to HA via an ester bond has surprising characteristics of compactness, elasticity and mechanical strength.

Example 17: Swelling Studies of (9) According to Irradiation Time

The swelling tests (SW) were conducted on hydrogels derived from compounds belonging to class (9), after 10 or 20 minutes' irradiation respectively. Swelling involves immersing the hydrogels in distilled water for a set time, and comparing the initial weights with the weight increase over time (due to absorption of water). The SW values are calculated according to the formula:

$$SW = \frac{\text{Weight}_{24h} - \text{Weight}_{initial}}{\text{Weight}_{initial}}$$

Figure 7:
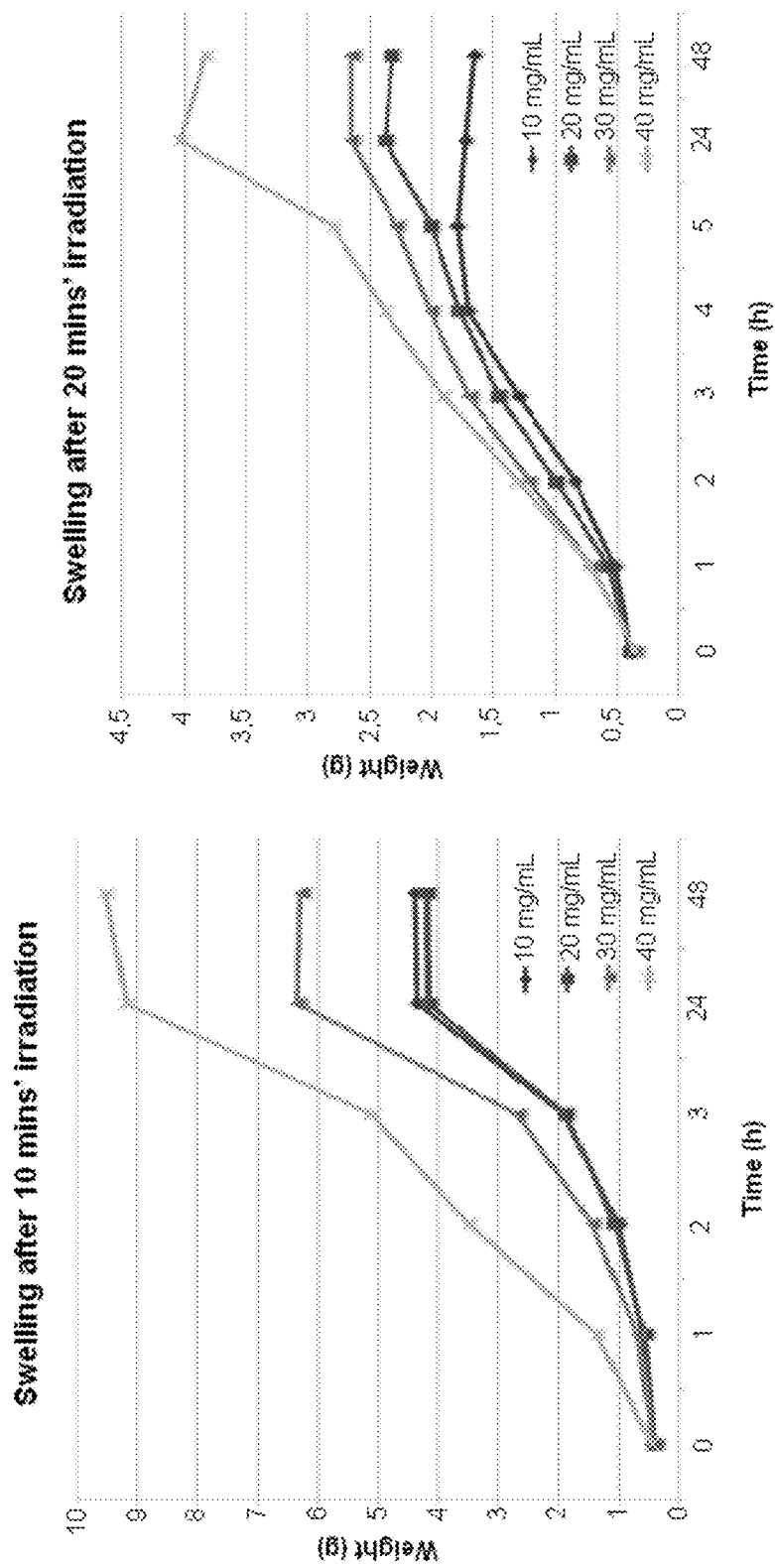
FIG. 7 shows the diagrams relating to the degree of swelling of hydrogels prepared as shown in Example 9.

FIG. 7 shows the diagrams relating to the degree of swelling of hydrogels prepared as shown in Example 9, obtained with the weight values recorded. Analysis of the graphics confirms what was stated above, namely that, concentration being equal, the duration of irradiation makes the hydrogel more compact, so that it absorbs less water, and conversely, irradiation times being equal, the compactness of the hydrogel increases with the concentration of the starting solution.

Example 18: Preparation of Sponges from Solutions with a Known Concentration of (9)

462.3 mg of HA ester derivative, obtained as described in Example 9, is dissolved in 23 ml of Milli-Q water, to obtain a solution with a concentration of 20 mg/ml. When solubilisation is complete, the solution is poured into a circular glass tray with a diameter of 7.7 cm.

Freeze-drying: the tray is transferred to the plates of a freeze-dryer, which are cooled to −3° C. The plates are maintained at said temperature for 4 hours, until the solution reaches the temperature of at least 2° C. The plates are then cooled to −35° C., and said temperature is maintained for 6 hours, until the solution is completely frozen. After cooling the condenser to a temperature of less than −35° C., the vacuum pump is switched on, and left running until the pressure in the chamber reaches a value lower than $1 \times 10^{-1}$ mbar. The plates are gradually heated to −5° C. in a period of 2 hours. When the set temperature has been reached, it is maintained for 24 hours. After that time, the plates are heated to 25° C., and the temperature thus reached is maintained for 6 hours. The sample obtained is inserted in a polystyrene Petri dish to protect it from humidity.

Irradiation: the sample is positioned under a Wood's lamp with an emission spectrum of between 330 and 380 nm for 12 hours. Every 3 hours the dish is inverted to allow irradiation of the whole surface of the sample.

The sponge thus obtained is uniformly porous and devoid of lamellae; when immersed in 30 mL of saline solution for 24 hours, both its shape and its texture remain unchanged. The sponge was also subjected to a plurality of squeezing and saturation cycles (at least 4): even under this stress situation, the sponge retained its shape, structure, elasticity and porosity unchanged, and therefore possesses shape memory.

The same sponge was then compared with a similar one prepared as described in Example 18 but not irradiated; the non-irradiated sponge disintegrated at soon as it came into contact with water.

The importance of both the ingredients and the process followed herein is further confirmed by that fact that another sponge was prepared in accordance with Example 18, but reversing the irradiation and freeze-drying steps. The solution obtained was therefore irradiated, and the resulting gel freeze-dried, under identical conditions to those described in Example 18; the resulting sponge dissolves when placed in water, giving rise to a compact gel.

Similarly to the hydrogels, the shape-memory sponges obtained were compared with similar ones prepared from HA bonded to umbelliferone via an ester bond, ie. without a spacer, as in Example 11.

Example 19: Preparation of Sponges from Solutions with a Known Concentration of (11)

462.3 mg of HA ester derivative, obtained as described in Example 11, is dissolved in 23 mL of Milli-Q water to obtain a solution at the concentration of 20 mg/mL. When solubilisation is complete, the solution is poured into a circular glass tray with a diameter of 7.7 cm.

The solution is subjected to freeze-drying and irradiation, exactly as in Example 18, and the resulting sponge is immersed in 30 ml of saline solution; it dissolves after a very short contact with the aqueous solution.

As already stated for hydrogels, it was also demonstrated for the sponges that shape memory properties (structure, elasticity and porosity) are surprisingly acquired only if a spacer is used to separate HA and umbelliferone, and only by following the precise process scheme detailed above.

Example 20: Swelling Studies of (15) Compared with an Equivalent Derivative Prepared as Described in Example 2 of EP1519962

The swelling tests (SW) were conducted on hydrogels prepared from the compound synthesised as described in example 15, and from the compound synthesised as described in Example 2 of patent EP1519962, at the concentration of 30 mg/mL and after 20 minutes' irradiation. The compound synthesised as described in Example 2 of EP1519962 is a derivative wherein the photocrosslinkable groups of propiophenone are bonded directly to HA via an ester bond, in a similar percentage to (15), namely about 50%.

By comparing the initial weights with the weight increase due to water absorption, the values of SW were calculated as described in example 17. FIG. 8 shows the diagrams obtained with the weight values recorded over time.

Analysis of the graph confirms that, degree of substitution being equal, the presence of the triethylene glycol spacer between HA and the photocrosslinking group produces hydrogels that absorb less water, and are therefore more compact; crosslinking is therefore more efficient. The product obtained as described in Example 2 of EP1519962 has absorbed nearly 50% more water than (15) after only an hour, and that trend continues over time. The hydrogel therefore has a very different texture from that obtained using the triethylene glycol spacer between HA and the photocrosslinking group, as described in the present invention. In the absence of a spacer, characteristics of compactness, elasticity and mechanical strength able to withstand compression and cutting, and shape memory, are not maintained.

Example 21: Rheological Characterisation of Hydrogels Prepared from (9)

The rheological measurements were taken at 25° C., in an oscillating regimen; in particular, only the modulus of elasticity G', which expresses the compactness of the hydrogel, and is therefore the fundamental parameter, was measured. G' (modulus of elasticity) was measured in Pa from 0.07 to 90.0 rad/s, with a force value of 10%. The values, obtained from samples gelled after irradiation with a low-powered UV lamp, were directly correlated with the crosslinking percentage, calculated by HPLC-MS analysis, assuming that the percentage of photopolymerisation was nil at t 0.

As will be seen from the diagram (FIG. 9), the trend of the modulus of elasticity G' (expressed in Pa at 0.628 rad/s), is proportional to that of the degree of crosslinking; solutions irradiated for a longer time are therefore more crosslinked, and consequently present better elastic properties, with higher G' values.

Example 22: Evaluation of Cell Proliferation on Human Fibroblast Cultures in the Presence of Hydrogels Prepared from (9)

The standard protocol for evaluation of cell proliferation involves the use of the MTT assay. Briefly, said assay quantitatively measures the presence of succinate dehydrogenase activity in cultured cells; said activities, which are only present in the mitochondria of viable cells, are normally used as markers to check on the metabolic activity, viability and consequently growth of cultured cells. The assay is based on conversion of the azolium dye MTT (3-(4,5-dimethylthiazol-2-yl)2,5 diphenyltetrazolium bromide) from yellow to blue, by succinate dehydrogenase. The amount of blue dye (formazan) determined spectrophotometrically is proportional to the presence of succinate dehydrogenase in the cell culture, and consequently proportional to the number of viable cells.

Human fibroblasts (HF), suspended in a suitable culture medium, were seeded in 24-well multiwell plates in the presence of (9) in solution at the concentration of 20 mg/mL or 30 mg/mL, and at increasing concentrations (20, 50, 100 µL) or, in the case of the control, with the medium only. The cells (HF) were incubated with an 0.5 mg/mL MTT solution for 3 hours at 37° C. At the end of the incubation the dye was extracted from the HF with an extracting solution (90% isopropanol, 10% DMSO), and read at the wavelength of 570 nm (OD, Optical Density).

The OD values at 570 nm are detected after 24 h (FIG. 10).

FIG. 10 shows that the solutions of HA derivative thus prepared are non-toxic, even in gradually increasing amounts, and maintain cell viability.

Example 23: Evaluation of Human Fibroblast Proliferation on Sponges Prepared as Described in Example 19

Human fibroblast (HF) suspensions were seeded on sponges prepared as described in example 19, and transferred to 24-well plates. 1 h after seeding, 1 mL of culture medium was deposited; the MTT assay was conducted after 3 and 7 days' culture (FIG. 11).

The control consisted of an equal amount of HF seeded in 24-well multiwell plates and treated with the culture medium only.

As can be seen from the chart (FIG. 11), the human fibroblasts seeded on the sponges are alive, viable and proliferating after 3 and 7 days' culture. Their viability is such as to induce greater proliferation than that of the control; proliferation is better in percentage terms after 3 days, but also considerable after 7 days. These results clearly demonstrate that sponges prepared as described in the present invention not only do not possess any toxicity towards cells, but actually promote cell proliferation. It should be borne in mind that during seeding on sponges and subsequent transfer to the wells, a number of cells are lost, so the proliferation values shown in FIG. 11 are even more surprising.

Example 24: Preparation of Hydrogels Deriving from Solutions of (9), with the Addition of Collagen in the w/w Ratio of 1:1

600 mg of HA ester derivative, obtained as described in Example 9, is dissolved in 20 mL of saline to obtain a solution at the concentration of 30 mg/mL. After complete solubilisation the pH is adjusted to weakly acid values (pH≈4) by gradual addition of 0.05 M HCl in an ice bath. 10 mL of acid solution of collagen from equine tendon, pre-prepared at the concentration of 60 mg/ml, is then added. After complete mixing the solution is microfiltered through an 0.2 µm filter, placed in a container and irradiated for a time t ranging between 3 and 15 minutes with a beam of light having a wavelength of 300-380 nm at room temperature.

A compact hydrogel able to maintain its shape after cutting or manipulation is obtained.

Example 25: Preparation of Sponges from Solutions with a Known Concentration of (9), with the Addition of Collagen in the w/w Ratio of 1:1

400.0 mg of HA ester derivative, obtained as described in Example 9, is dissolved in 20 mL of Milli-Q water to obtain a solution at the concentration of 20 mg/mL. After complete solubilisation the pH is adjusted to weakly acid values (pH≈4) by gradual addition of 0.05 M HCl in an ice bath. 10 mL of acid solution of equine tendon collagen, pre-prepared at the concentration of 40 mg/ml, is then added. After complete mixing the solution is microfiltered through an 0.2 µm filter, and poured into a circular glass tray with a diameter of 5.0 cm.

The solution is freeze-dried and irradiated as described in Example 19. The resulting sponge, immersed in 30 mL of saline solution, does not dissolve or disintegrate, even after lengthy contact (72-96 h) with the aqueous solution, and possesses shape-memory properties similar to those of the sponges described in Example 20.

Example 26: Preparation of Sponges from Solutions with a Known Concentration of (9), with the Addition of Collagen in the w/w Ratio of 1:4

400.0 mg of HA ester derivative, obtained as described in Example 9, is dissolved in 20 mL of Milli-Q water to obtain a solution at the concentration of 20 mg/mL. After complete solubilisation the pH is adjusted to weakly acid values (pH≈4) by gradual addition of 0.05 M HCl in an ice bath. 10 mL of acid solution of equine tendon collagen, pre-prepared at the concentration of 160 mg/ml, is then added. After complete mixing the solution is microfiltered through an 0.2 µm filter, and poured into a circular glass tray with a diameter of 5.0 cm.

The solution is freeze-dried and irradiated as described in Example 19. The resulting sponge, immersed in 30 mL of saline solution, does not dissolve or disintegrate, even after lengthy contact (72-96 h) with the aqueous solution.

The sponge retains the shape memory of the sponges described in Example 20, retaining its structure and elasticity even after mechanical stresses. In view of the factors described and demonstrated herein, the Applicant intends to claim hydrogels and sponges, both with shape memory, consisting of umbelliferone or propiophenone bonded to PEG via an ether bond, and the resulting product, bonded in turn to hyaluronic acid via an ester or amide bond; it also intends to claim the hydrogel preparation process involving solubilisation of the compounds and subsequent irradiation of the solutions obtained, and the sponge preparation process involving solubilisation of the starting compounds, freeze-drying of the solutions and subsequent irradiation. Both hydrogels and sponges are suitable for use in the medical, cosmetic and dermocosmetic fields, either used alone or combined with pharmacologically and/or biologically active substances, or with cells. In particular, both are suitable for use in the following specific applications:
intra-articular treatment of osteoarthritis and cartilage damage,
release of active ingredients,
coating of objects for medical use,
filling of soft tissues,
in the prevention of postoperative adhesions, and filling of deep cavitated lesions following surgery.

The invention claimed is:

1. Photo-crosslinked derivatives of hyaluronic acid (HA) consisting of HA, a polyethylene glycol (PEG) bifunctional spacer which is triethylene glycol, and a photoreactive compound selected from coumarin derivatives,
wherein the coumarin derivative is selected from umbelliferone, aesculetin, scopoletin, psoralens, furanocoumarin and dicoumarol,
the bond between the bifunctional spacer and HA is an ester, and
wherein the photo-crosslinked derivatives are in the form of shape-memory hydrogels or shape-memory sponges.

2. Derivatives according to claim 1, wherein the bond between the photoreactive compound and the bifunctional spacer is an ether bond.

3. Derivatives according to claim 1, wherein HA has a weight-average MW of between 40 kDa and 700 kDa.

4. Derivatives according to claim 1, further comprising pharmacologically and/or biologically active substances selected from trophic factors, antibiotics, steroidal and non-steroidal anti-inflammatory drugs, proteins, peptides, hormones, platelet extracts or differentiated and/or undifferentiated cells.

5. Derivatives as claimed in claim 1, further comprising collagen.

6. Process for the preparation of derivatives according to claim 1, in the form of shape-memory hydrogels, comprising the following steps:
 a. formation of an ether bond between triethylene glycol and coumarin derivative;
 b. formation of an ester bond between the product obtained in step a) and HA, with a final degree of derivatisation of HA varying from 5 to 80 mol %;
 c. solubilisation of the product obtained in step b) and irradiation of the resulting isotonic aqueous solution with UV light at a wavelength between 300 and 450 nm, for a time ranging from 1 minute to 24 hours.

7. Process for the preparation of derivatives according to claim 1, in the form of shape-memory sponges, comprising the following steps:
 a. formation of an ether bond between triethylene glycol and coumarin derivative;
 b. formation of an ester bond between the product obtained in step a) and HA, with a final degree of derivatisation of HA varying from 5 to 80 mol %;
 b') solubilisation of the product obtained in step b) in an isotonic aqueous solution and freeze-drying of the isotonic aqueous solution thus obtained;
 c. irradiation of the freeze-dried product obtained in step b') with UV light at a wavelength between 300 and 450 nm, for a time ranging from 1 minute to 24 hours.

8. Process for the preparation of derivatives as claimed in claim 6, further comprising a step of collagen addition before the HA irradiation step.

9. Photo-crosslinked derivatives of hyaluronic acid in the form of shape-memory hydrogels according to claim 1 for use in the intra-articular treatment of osteoarthritis and cartilage damage.

10. Photocrosslinked derivatives of hyaluronic acid in the form of shape-memory hydrogels according to claim 1 for use in the release of active ingredients, coating of objects for medical use, filling of soft tissues, and prevention of post-surgical adhesions.

11. Photocrosslinked derivatives of hyaluronic acid in the form of shape-memory hydrogels as claimed in claim 1, for use in filling deep cavitated postoperative lesions.

12. Photo-crosslinked derivatives of hyaluronic acid in the form of shape-memory sponges according to claim 1 for use in the intra-articular treatment of osteoarthritis and cartilage damage.

13. Photo-crosslinked derivatives of hyaluronic acid in the form of shape-memory sponges, according to claim 1, for use in the release of active ingredients, coating of objects for medical use, filling of soft tissues, and prevention of post-surgical adhesions.

14. Photocrosslinked derivatives of hyaluronic acid in the form of shape-memory sponges as claimed in claim 1, for use in the filling of deep cavitated postoperative lesions.

15. Medical device comprising at least one photocrosslinked derivative according to claim 1.

16. Derivatives according to claim 1 wherein the coumarin derivative is umbelliferone.

17. Derivatives according to claim 3, wherein HA has a weight-average MW of between 160 and 220 kDa.

18. Derivatives as claimed in claim 5 wherein said collagen is native and/or hydrolysed collagen.

19. Process as claimed in claim 6, wherein irradiation of the resulting isotonic aqueous solution with UV light is at a wavelength between 320 and 380 nm.

20. Process as claimed in claim 7, wherein irradiation of the freeze-dried product obtained in step b') with UV light is at a wavelength between 320 and 380 nm.

* * * * *